(12) United States Patent
Isobe

(10) Patent No.: US 7,662,555 B2
(45) Date of Patent: *Feb. 16, 2010

(54) METHOD FOR DETECTING BIOMOLECULE, LABELING DYE USED THEREFORE, AND LABELING KIT

(76) Inventor: Shinichiro Isobe, 27-10 Mukaishinmachi 2-chome, Minami-ku, Fukuoka-shi (JP) 811-1345

( * ) Notice: Subject to any disclaimer, the term of this patent is extended or adjusted under 35 U.S.C. 154(b) by 204 days.

This patent is subject to a terminal disclaimer.

(21) Appl. No.: 10/584,089

(22) PCT Filed: Dec. 22, 2004

(86) PCT No.: PCT/JP2004/019215

§ 371 (c)(1),
(2), (4) Date: Aug. 9, 2006

(87) PCT Pub. No.: WO2005/062046

PCT Pub. Date: Jul. 7, 2005

(65) Prior Publication Data

US 2007/0154890 A1 Jul. 5, 2007

(30) Foreign Application Priority Data

Dec. 24, 2003 (JP) ............................. 2003-427268

(51) Int. Cl.
*C12Q 1/68* (2006.01)
*C12P 19/34* (2006.01)
*C07H 21/00* (2006.01)
*C07H 21/02* (2006.01)

(52) U.S. Cl. .................... 435/6; 435/91.1; 536/23.1; 536/24.3; 536/26.6

(58) Field of Classification Search ............ 435/6, 435/91.1; 536/23.1, 24.3, 26.6
See application file for complete search history.

(56) References Cited

U.S. PATENT DOCUMENTS

| | | | |
|---|---|---|---|
| 5,075,215 A | 12/1991 | Dreyer | |
| 5,132,206 A | 7/1992 | Dreyer | |
| 6,048,687 A | 4/2000 | Kenten et al. | |
| 6,482,640 B1 | 11/2002 | Tanaka et al. | |
| 7,015,002 B2 * | 3/2006 | Isobe | 435/6 |
| 2002/0037589 A1 | 3/2002 | Gupta et al. | |
| 2002/0064782 A1 | 5/2002 | Shinoki et al. | |
| 2003/0003484 A1 | 1/2003 | Fagan | |
| 2003/0073126 A1 | 4/2003 | Neuenhofer et al. | |
| 2003/0114399 A1 | 6/2003 | Blakely et al. | |
| 2003/0214228 A1 | 11/2003 | Itou | |

FOREIGN PATENT DOCUMENTS

| | | |
|---|---|---|
| EP | 1 148 119 | 10/2001 |
| EP | 1 152 008 | 11/2001 |
| EP | 0 722 508 | 4/2003 |
| EP | 1 303 751 | 8/2005 |
| JP | 9-505464 | 6/1997 |
| JP | 2001-153870 | 6/2001 |
| JP | 2001-288197 | 10/2001 |
| JP | 2002-060744 | 2/2002 |
| JP | 2002-161135 | 6/2002 |
| JP | 2002-173673 | 6/2002 |
| JP | 2003-532790 | 11/2003 |
| JP | 2004-187563 | 7/2004 |
| WO | 95/08644 | 3/1995 |
| WO | 96/36731 | 11/1996 |
| WO | 98/29736 | 7/1998 |
| WO | 01/38482 | 5/2001 |
| WO | 01/86264 | 11/2001 |

OTHER PUBLICATIONS

Iyer, V. et al., "The Transcriptional Program in the Response of Human Fibroblasts to Serum", *Science*, vol. 283, pp. 83 to 87 (1999).
Stojanovic, M. et al., "Aptamer-Based Folding Fluorescent Sensor for Cocaine", *J. Am. Chem. Soc.*, vol. 123, pp. 4928 to 4931 (2001).
Ueyama, H. et al., "A Novel Potassium Sensing in Aqueous Media with a Synthetic Oligonucleotide Derivative. Fluorescence Resonance Energy Transfer Associated with Guanine Quartet- Potassium Ion Complex Formation", *J. Am. Chem,. Soc.*, vol. 124, pp. 14286 to 14287 (2002).
Walkup, G. et al., "Design and Evaluation of a Peptidyl Fluorescent Chemosensor for Divalent Zinc", *J. Am. Chem. Soc.*, vol. 118, pp. 3053 to 3054 (1996).
Indian Office Action issued Nov. 7, 2008 in corresponding Indian Application No. 2338/CHENP/2006.
European Office Action issued Sep. 9, 2009 in corresponding Application No. 04 807 572.5.
Chinese Office Action issued Jul. 17, 2009 in corresponding Application No. 200480038772.9, with English translation.
Indian Office Action issued Jul. 17, 2009 in corresponding Application No. 233/CHENP/2006.

* cited by examiner

*Primary Examiner*—Jezia Riley
(74) *Attorney, Agent, or Firm*—Wenderoth, Lind & Ponack, L.L.P.

(57) ABSTRACT

The present invention provides a method for detecting a biomolecule. The method includes reacting a biomolecule sample with an organic EL-dye and measuring the fluorescence of the biomolecule sample labeled with the organic EL-dye. The method provides a highly sensitive method of detecting a biomolecule at lower cost.

16 Claims, 8 Drawing Sheets

(a)(b)(c)(d)(e)

METHOD FOR DETECTING BIOMOLECULE, LABELING DYE USED THEREFORE, AND LABELING KIT

TECHNICAL FIELD

The present invention relates to a method of detecting a biomolecule such as nucleic acids, proteins, peptides, saccharides and the like using a fluorescence dye, and a labeling dye and a labeling kit used for the detection method.

BACKGROUND ART

Recently, post genome researches have been intensively and world widely done aiming for specific gene analysis: technologies, gene therapies and tailor made medical treatments. As for the gene analysis technology, a method of detecting DNA using a DNA microarray, for example, is used. According to this detection method, simultaneous analysis of expression, functionality, mutation and the like of a plurality of genes can be conducted simply and quickly.

In the detection method using a DNA microarray, DNA chips obtained by spot-fixing many sequences (probe nucleic acids) of DNA or oligonucleotide on a substrate made of glass, silicon or the like are used. By hybridization of a probe nucleic acid fixed on a substrate with a labeled sample RNA or DNA (target nucleic acid), a labeled nucleic acid having base sequence complimentary to that of the probe nucleic acid is selectively bound to the probe nucleic acid. After drying of the microarray, the fluorescence intensity of the labeled target nucleic acid is measured.

A fluorescence dye is widely used for labeling. High fluorescence intensity, emission even under dry conditions (solid conditions), water solubility, and the like are required for the fluorescence dye. As the fluorescence dye, for example, Cy3 and Cy5 are used (see, e.g., Science 283, 1 Jan. 1999, pp. 83-87).

DISCLOSURE OF INVENTION

However, although Cy3 and Cy5 manifest high fluorescence intensity and have a merit of emission even in solid state, they are very expensive, leading inevitably to a highly expensive detection method. Also, there is a problem that the ratio of incorporation into a sample RNA or DNA is low and sufficient labeling of a sample RNA or DNA is impossible, resultantly, detection sensitivity is not sufficient. In contrast, fluorescence dye replacing Cy3 and Cy5 is not found to date.

An object of the present invention is to solve the above-mentioned problems and to provide a highly sensitive method of detecting a biomolecule at lower cost.

The present inventors have found that an organic EL (electroluminescence)-dye used in an organic EL element manifests high fluorescence intensity when used as a label of a biomolecule, in a process of searching for fluorescence dyes replacing Cy3 and Cy5, and achieved the present invention.

Namely, the method of detecting a biomolecule according to the present invention is characterized by that it includes reacting a biomolecule sample with an organic EL-dye and measuring the fluorescence of the biomolecule sample labeled with the organic EL-dye. In the present invention, the biomolecule means a molecule species present in an organism, and includes those constituting the structure of an organism, those being concerned in production and conversion of energy, those ruling bioinformation, and the like. Specifically included are nucleic acids, proteins, saccharides, lipids, peptides, nucleotides, metabolic intermediates and metabolic enzymes, hormones, and neurotransmitters, and the like.

Between an organic EL-dye and a biomolecule, an amide bond, imide bond, urethane bond, ester bond, guanidine bond or thiourea bond can be formed. Prior to reaction with a biomolecule, any one reactive group selected from the group consisting of an isocyanate group, isothiocyanate group, epoxy group, halogenated alkyl group, triazine group, carbodiimide group and active ester carbonyl group can be introduced in the above-mentioned organic EL-dye. Further, any one selected from the group consisting of nucleic acids, proteins, peptides and saccharides can be used as the biomolecule sample.

The method of detecting a biomolecule according to the present invention is characterized by that it includes labeling of a biomolecule sample with a labeling dye comprising a 5-membered ring compound having a conjugate system and containing one or more hetero atom(s), selenium atom(s) or boron atom(s) and measurement of the fluorescence of the labeled biomolecule sample.

Also, a condensed poly-ring compound consisting of the above-mentioned 5-membered ring compound and a 6-membered ring compound having a conjugate system may be used. Further, an azole derivative or imidazole derivative can be used as the 5-membered ring compound. Prior to reaction with the above-mentioned biomolecule, any one reactive group selected from the group consisting of an isocyanate group, isothiocyanate group, epoxy group, halogenated alkyl group, triazine group, carbodiimide group and active ester carbonyl group can be introduced in an organic EL-dye.

The labeling dye according to the present invention is characterized by that it is a labeling dye used for detection of a biomolecule by measurement of fluorescence, wherein the dye includes an organic EL-dye having a reactive group to bind to a biomolecule. As the reactive group, any one functional group selected from the group consisting of a carboxyl group, isocyanate group, isothiocyanate group, epoxy group, halogenated alkyl group, triazine group, carbodiimide group and active ester carbonyl group can be used. As the organic EL-dye, a compound comprising a 5-membered ring compound having a conjugate system and containing one or more hetero atom(s), selenium atom(s) or boron atom(s) can be used. Further, a condensed poly-ring compound consisting of the above-mentioned 5-membered ring compound and a 6-membered ring compound having a conjugate system may also be used. Furthermore, an azole derivative or imidazole derivative may be used as the 5-membered ring compound.

The labeling kit for a biomolecule according to the present invention is characterized by that it includes an organic EL-dye for labeling a biomolecule. As the biomolecule, any one selected from the group consisting of nucleic acids, proteins, peptides and saccharides can be used. As the reactive group for the biomolecule, any one functional group selected from the group consisting of a carboxyl group, isocyanate group, isothiocyanate group, epoxy group, halogenated alkyl group, triazine group, carbodiimide group and active ester carbonyl group can be used. As the organic EL-dye, a compound comprising a 5-membered ring compound having a conjugate system and containing one or more hetero atom(s), selenium atom(s) or boron atom(s) can be used. Further, a condensed poly-ring compound consisting of the above-mentioned 5-membered ring compound and a 6-membered ring compound having a conjugate system may also be used. Furthermore, an azole derivative or imidazole derivative may be used as the 5-membered ring compound.

The another method of detecting a biomolecule according to the present invention is characterized by that the method comprises of reacting a biomolecule sample and a probe labeled with an organic EL-dye and measuring the fluorescence of the labeled biomolecule. The above biomolecule can include a nucleic acid while the above probe can include an oligonucleotide or PNA having base sequence(s) complementary to the base sequence of the nucleic acid. Alternatively, when the above oligonucleotide is a primer or terminator, a method of measuring fluorescence of the product by amplifying the above nucleic acid can be used. Alternatively, the primer can be labeled with an organic EL-dye prior to amplifying the nucleic acid. Furthermore, the above oligonucleotide or PNA can be comprised of a molecular beacon.

The another method of detecting a biomolecule according to the present invention is characterized by that the method comprises of size separating a biomolecule sample by electrophoresis, wherein the biomolecule sample is labeled with an organic EL-dye prior to the electrophoresis or after the electrophoresis. The biomolecule sample is a nucleic acid, and base sequence(s) of the nucleic acid can be determined based on the electrophoresis image of the labeled nucleic acid. Alternatively, the biomolecule sample is a protein, and the protein removed from the sample based on the electrophoresis image can be identified by mass analysis.

For example, when used as a kit of DNA microarray, a nucleic acid is used as the biomolecule sample and a probe nucleic acid is fixed on a microarray, while the target nucleic acid sample is labeled by reaction with an organic EL-dye, and the labeled target nucleic acid is spotted on the microarray and hybridization can be conducted under this conditions. Further, applying a binding property between avidin (streptavidin) and biotin, the avidin modified with this dye can be used as a biological assay kit for ELISA (enzyme-linked immunosorbent assay), Western blotting and the like. It can also be used as a kit for protein array.

The dyeing method according to the present invention is characterized by that the method comprises of labeling a biomolecule of tissues or cells with an organic EL-dye. The above biomolecules may include a nucleic acid or protein.

The chromatic dye used for dyeing tissues or cells according to the present invention is characterized by that the dye comprises of an organic EL-dye having reactive groups to bind with a biomolecule of tissues or cells.

According to the present invention, use of an organic EL-dye as a labeling dye for a biomolecule gives the following effects.

That is, an organic EL-dye shows high quantum yield in solid state (including solid state and semi-solid state) and manifests high fluorescence intensity. Since an organic EL-dye is cheap as compared with Cy3 and Cy5, a biomolecule can be detected at lower cost. Further, an organic EL-dye reacts with a biomolecule almost quantitatively and shows high incorporation ratio, therefore, high detection sensitivity can be obtained. Furthermore, use of said dye increases the degree of freedom of selectivity of fluorescence wavelength, and multiple fluorescence wavelengths of orange, yellow, green, blue and the like can be used. By this, it becomes possible to use two or more fluorescence dyes having large stokes shift (large difference between excited wavelength and fluorescence wavelength), consequently, plural target nucleic acids contained in one sample can also be simultaneously detected. While Cy3 and Cy5 need to be kept in refrigerated state, an organic EL-dye is chemically stable and can be kept for a long time at ambient temperature, therefore, handling thereof is easy.

BEST MODE FOR CARRYING OUT THE INVENTION

Figure 1A:
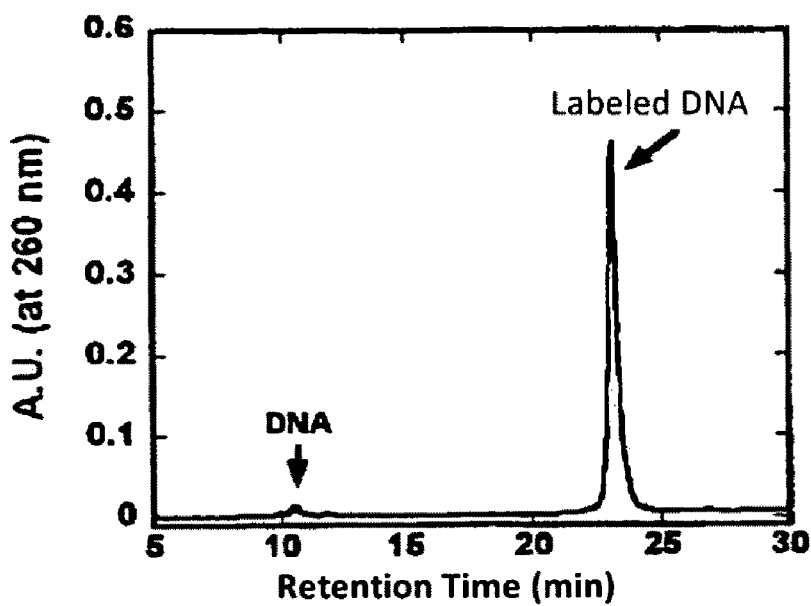
FIG. 1A shows one example of the HPLC profile of a labeled oligonucleotide in Example 1 of the present invention.

Hereafter, embodiments of the present invention will be explained in detail.

The organic EL-dye used in the present invention is not particularly limited provided it is a dye sandwiched in solid state between a pair of anode and cathode and capable of emitting by virtue of energy in recombination of a hole injected from an anode and an electron injected from a cathode. For example, poly-ring aromatic compounds such as tetraphenylbutadiene, perylene and the like, cyclopentadiene derivatives, distyrylpyrazine derivatives, acridone derivatives, quinacridone derivatives, stilbene derivatives, phenothiazine derivatives, pyradinopyridine derivatives, azole derivatives, imidazole derivatives, carbazole derivatives, tetraphenylthiophene derivatives and the like can be used. Further, a dye having a carboxyl group in the molecule or into which a carboxyl group can be introduced is preferable. The reason for this is that a reactive group for bonding with a biomolecule can be introduced easily as described below.

It is preferable that the organic EL-dye has a reactive group for bonding with a biomolecule sample (hereinafter, referred to target molecule) and the reactive group has a functional group capable of reacting with an amino group, imino group, thiol group, hydroxyl group, carboxyl group or aldehyde group of the target molecule. It is preferable that an amide bond, imide bond, urethane bond, ester bond, guanidine bond or thiourea bond is formed between an organic EL-dye and a biomolecule. As the functional group, for example, an isocyanate group, isothiocyanate group, epoxy group, halogenated sulfonyl group, acyl chloride group, halogenated alkyl group, glyoxal group, aldehyde group, triazine group, carbodiimide group and active ester carbonyl group and the like may be used. It is preferable that any one selected from the group consisting of an isocyanate group, isothiocyanate group, epoxy group, halogenated alkyl group, triazine group, carbodiimide group and active ester carbonyl group is used. The reason for this is that it can form an amide bond with an amino group in a target molecule and can directly bind to an imino group in a biomolecule. Further preferable is a triazine group, carbodiimide group or active ester carbonyl group. When these organic EL-dyes have a carboxyl group, an amino group and imino group present in a biomolecule can also be modified directly in the presence of a carbodiimide derivative and triazine derivative. Further, an organic EL-dye having a triazine group with an optional substituent or a carbodiimide group with an optional substituent can react directly with an imino group of guanine and thymine in DNA bases, therefore, introduction of a dye by a PCR (polymerase chain reaction) method is not necessary, and application thereof to mismatch detection and the like is possible.

For example, as the active ester carbonyl group, N-hydroxysuccinimide ester and maleimide ester can be used. By use of N-hydroxysuccinimide, an EL-dye and a target molecule can be bound by an amide bond via an N-hydroxysuccinimide ester using N,N'-dicyclohexylcarbodiimide (DCC) as a condensing agent, as shown in formula I in the following Scheme 1. Further, as shown in formula II in the Scheme 1, a triazine derivative can also be used as the active ester carbonyl group. As the carbodiimide group, carbodiimide reagents such as DCC and 1-cyclohexyl-3-(2-morpholinoethyl)carbodiimide and the like can be used. An EL-dye and a target molecule can be bound by an amide bond via a carbodiimide (formula III). Further, an EL-dye having previously a carbodiimide group or triazine group in the molecule can also be bound directly to an amino group and imino group in a biomolecule (formula IV).

Furthermore, excitation wavelength and emission wavelength can be changed by changing a substituent on an organic EL-dye, therefore, a plurality of samples can also be simultaneously detected by virtue of a plurality of colors.

Scheme 1

Formula 1

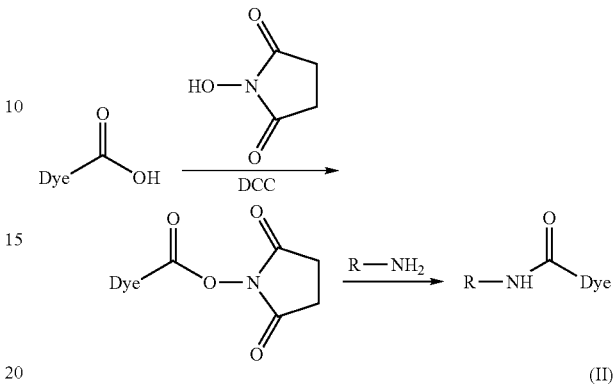

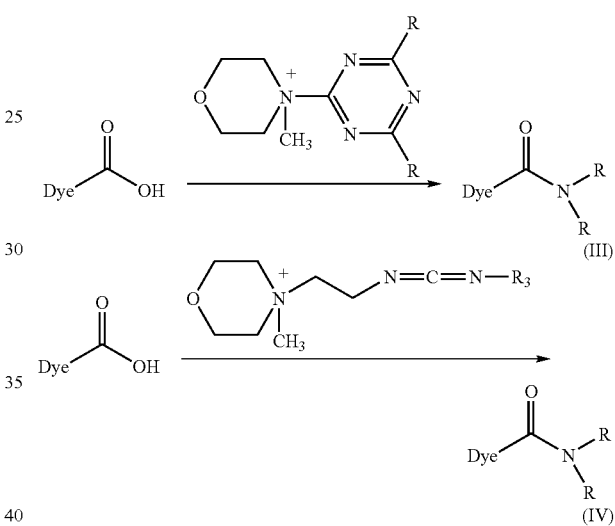

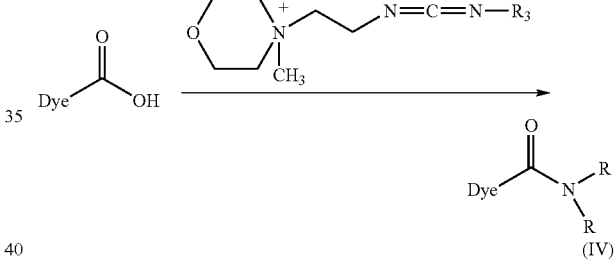

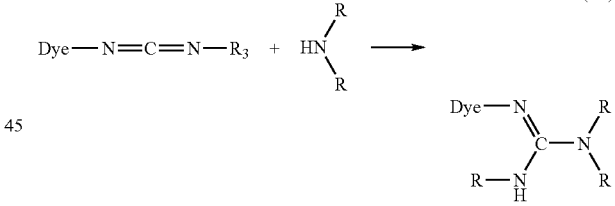

A reactive group can be bound with an amino residue modified at the end of oligo DNA when the target molecule is DNA, with amino residue in the case of a protein, an amino group of a polypeptide, for example, an amino residue of a polylysine derivative in the case of peptides, and with an amino group in a polysaccharide derivative skeleton in the case of a polysaccharide.

As the preferable organic EL-dye used in the detection method of the present invention, the compounds being comprised of a 5-membered ring compound having a conjugate system and containing one or more hetero atom(s), selenium atom(s) or boron atom(s) are given. Further specifically, a mono-ring compound composed of a 5-membered ring compound having a conjugate system, and a condensed poly-ring compounds consisting of 6-membered ring compound having a conjugate system and the 5-membered ring compound are given. The reason for this is that they have large quantum yield and show intense fluorescence even in solid state.

Specific examples of the condensed poly-ring compound are explained below.

(Mono-Azole Derivative 1)

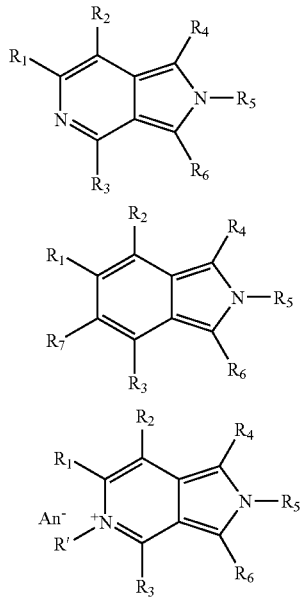

Formula 2

(wherein, $R_1$, $R_2$, $R_3$, $R_4$, $R_6$ and $R_7$ represent each independently an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_1$, $R_2$, $R_3$, $R_4$, $R_6$ and $R_7$ may be the same or different. R' represents an alkyl group optionally having an aromatic ring, aliphatic hydrocarbon group such as alkenyl group or aromatic hydrocarbon group. An- represents halide ions such as Cl—, Br— and I—, $CF_3SO_3$—, BF4- or PF6-.) These are the same also in the following general formulae unless otherwise stated.

(Mono-Azole Derivative 2)

Formula 3

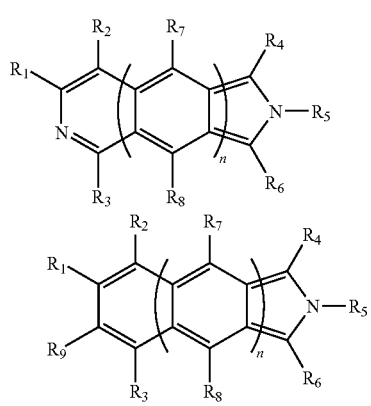

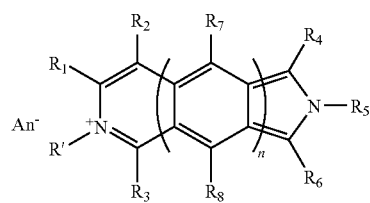

(wherein, $R_8$ and $R_9$ represent each an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_8$ and $R_9$ may be the same or different.) These are the same also in the following general formulae unless otherwise stated. (wherein, n represents an integer of 1 or more, preferably of 1 to 5.) This is the same also in the following general formulae.

(Diazole Derivative 1)

Formula 4

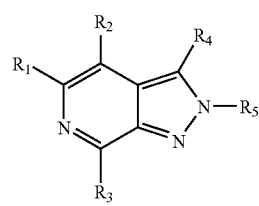

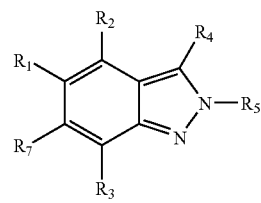

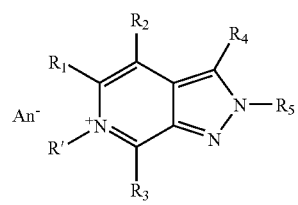

(Diazole Derivative 2)

Formula 5

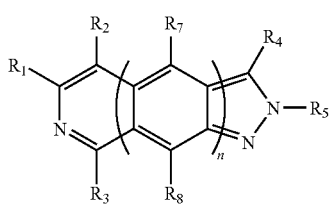

-continued

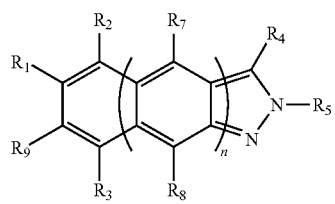

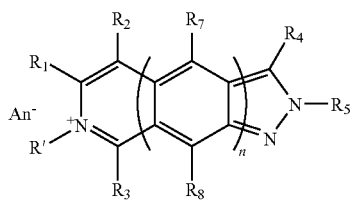

(Diazole Derivative 3)

Formula 6

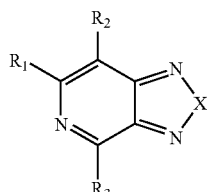

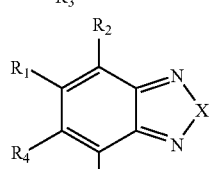

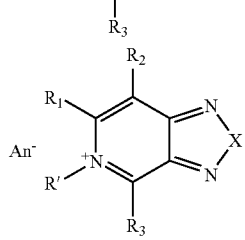

(wherein, $R_1$, $R_2$, $R_3$ and $R_4$ represent each independently an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_1$, $R_2$, $R_3$, $R_4$, $R_6$ and $R_7$ may be the same or different. As $R_2$ and $R_3$, aromatic hydrocarbon groups optionally having a substituent are preferable, and as this substituent, alkyl groups and alkoxy groups having 1 to 4 carbon atoms, or a bromine atom are preferable. Further, as the alkyl group, a methyl group, and as the alkoxy group, a methoxy group, are preferably used, respectively. X represents a nitrogen atom, sulfur atom, oxygen atom, selenium atom or boron atom, optionally having a substituent.) This is the same also in the following general formulae unless otherwise stated.

(Diazole Derivative 4)

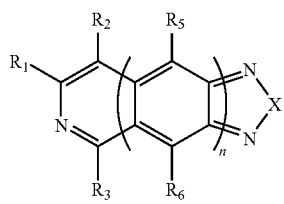
Formula 7

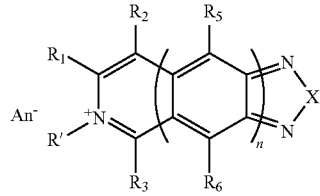

(Diazole Derivative 5)

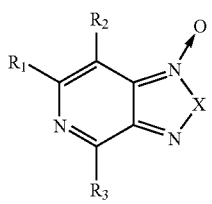
Formula 8

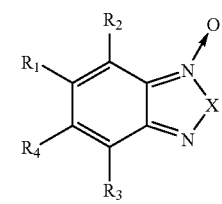

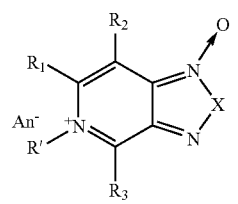

(wherein, N→O represents a state in which a nitrogen atom is coordinate-bonded to an oxygen atom.)

(Diazole Derivative 6)
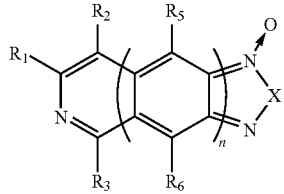
Formula 9
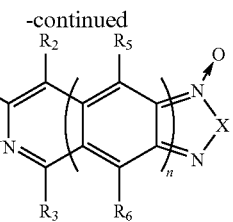
(Diazole Derivative 7)
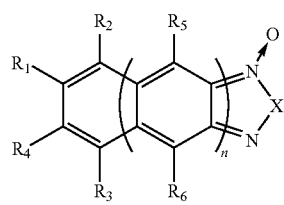
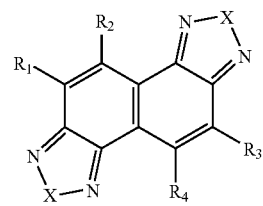
Formula 10
(Diazole Derivative 8)
Formula 11-1
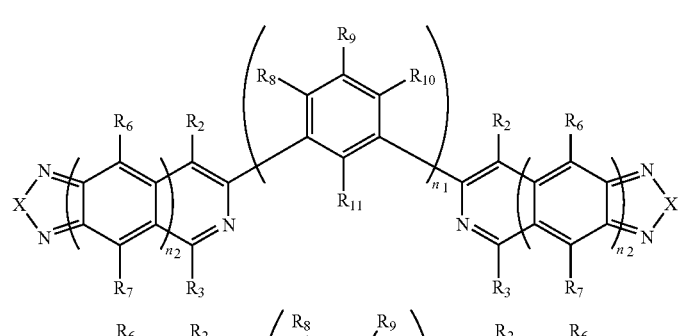
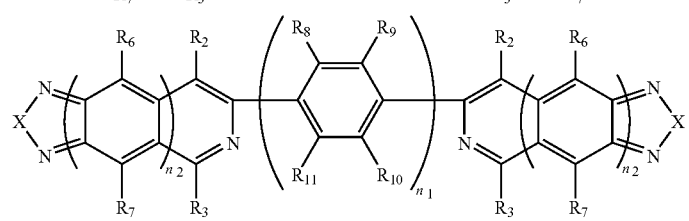
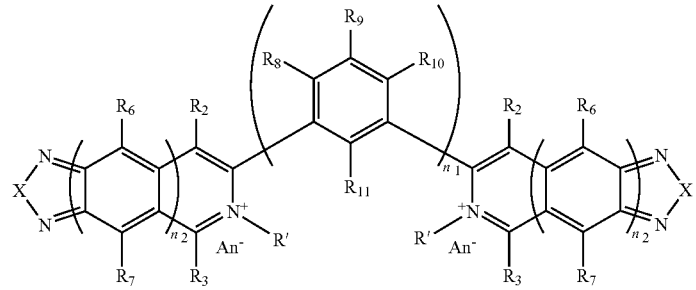
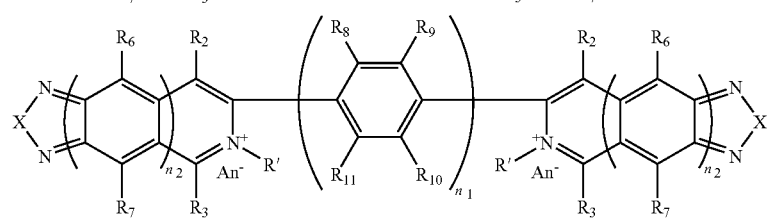

-continued

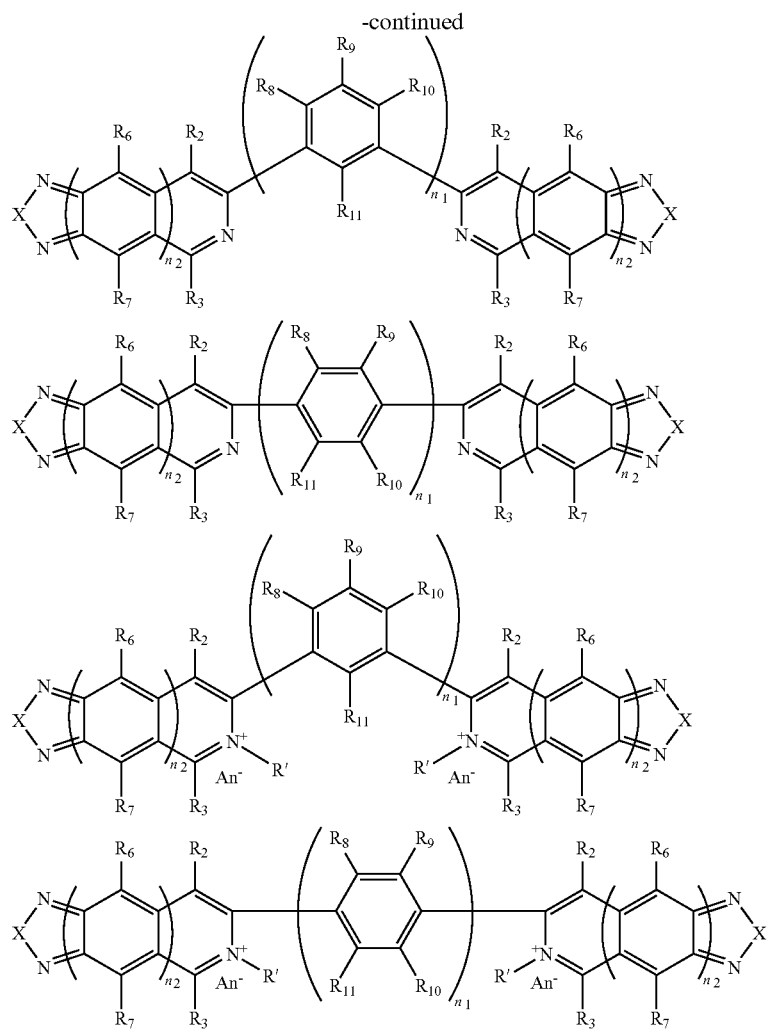

Formula 11-2

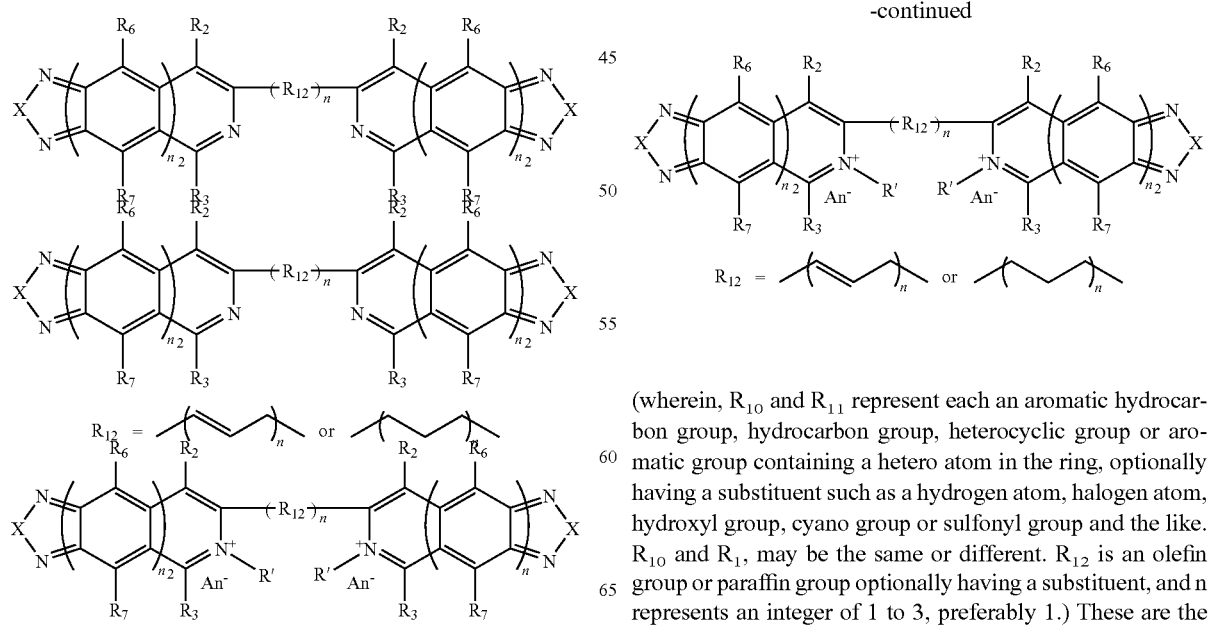

(wherein, $R_{10}$ and $R_{11}$ represent each an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_{10}$ and $R_1$, may be the same or different. $R_{12}$ is an olefin group or paraffin group optionally having a substituent, and n represents an integer of 1 to 3, preferably 1.) These are the same in the following formulae unless otherwise stated.

(Diazole Derivative 9)
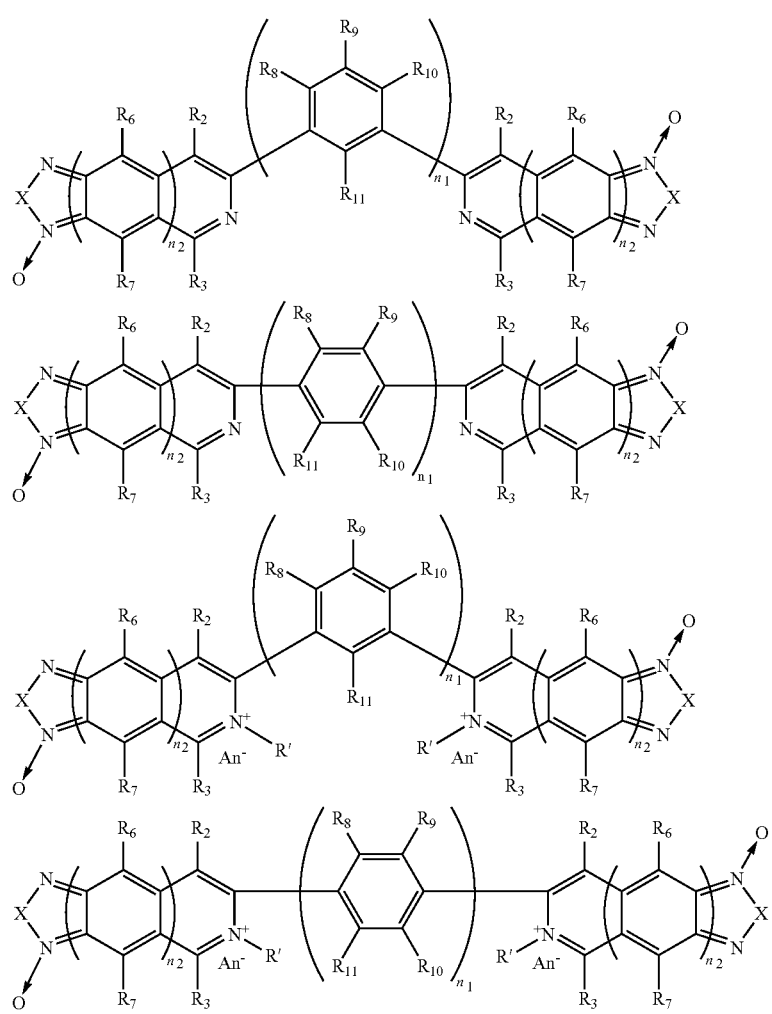
Formula 12-1
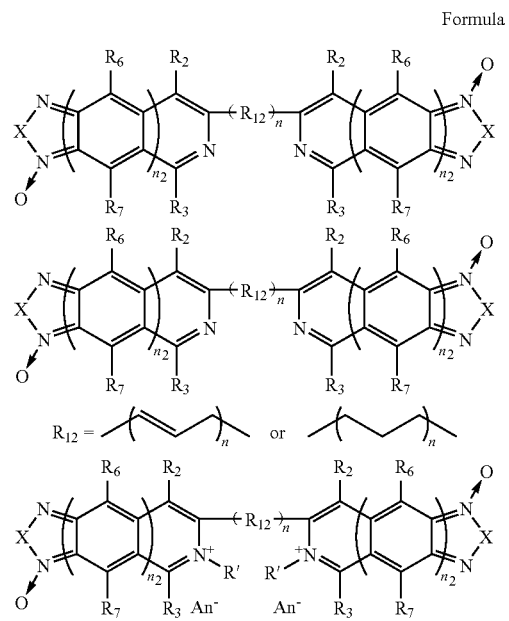
Formula 12-2
The above-mentioned diazole derivatives are not particularly limited, but an oxadiazolopyridine derivative of the following general formula can be suitably used.
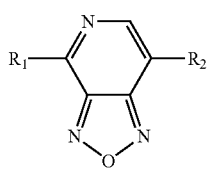
Formula 13
Regarding the oxazolopyridine derivative, its carboxylic acid derivative is synthesized, then, it is derived into an active ester containing N-hydroxysuccinimide ester using N,N'-dicyclohexylcarbodiimide (DCC) as a condensing agent, for example, according to a reaction shown in the following Scheme 2, and the resulting derivative is used.

Scheme 2

Formula 14

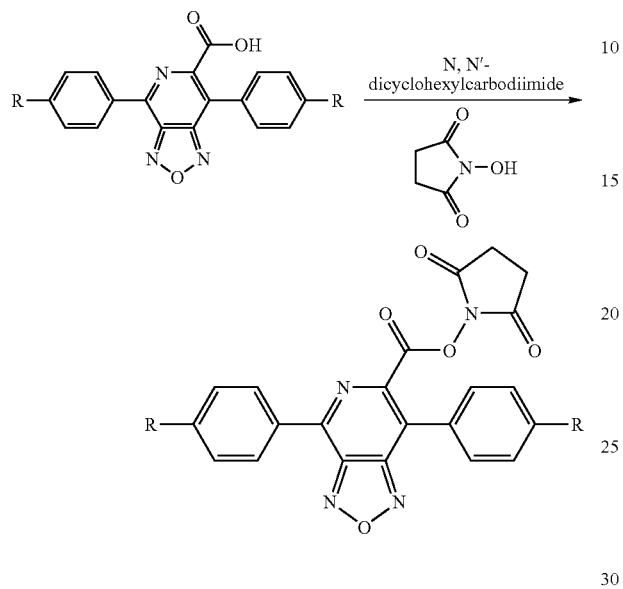

(Triazole Derivative 1)

Formula 15

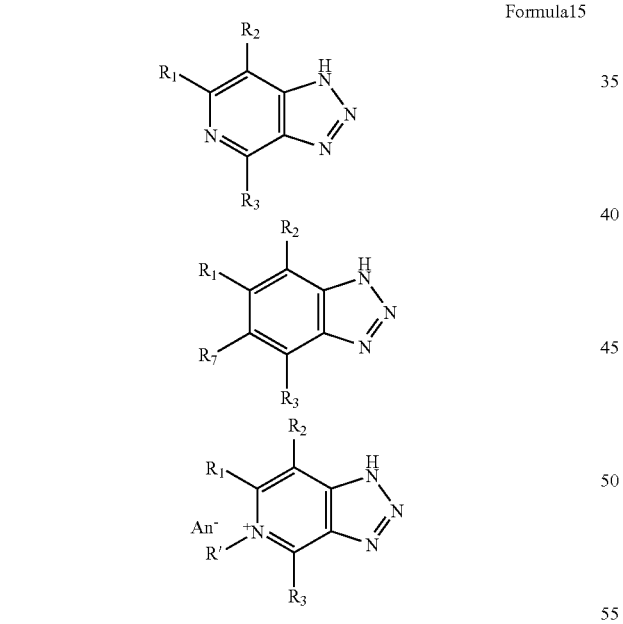

(Triazole Derivative 2)

Formula 16

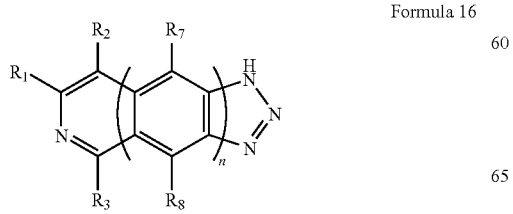

-continued

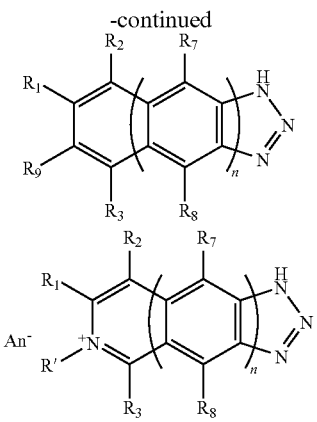

As the 5-membered ring compound, the following derivatives containing a thiophene group can also be used.

(Thiophene Derivative 1)

Formula 17

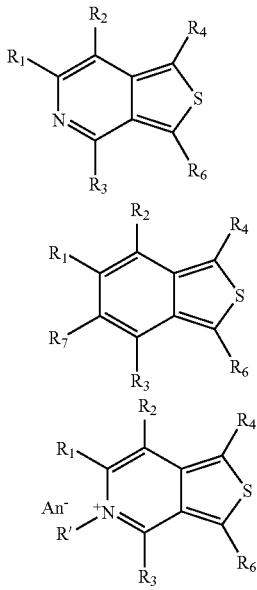

(Thiophene Derivative 2)

Formula 18

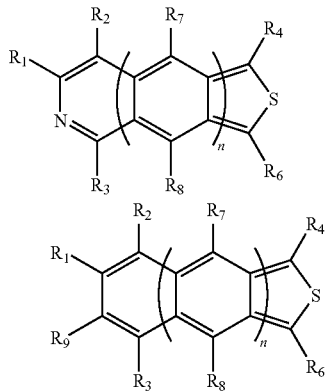

-continued

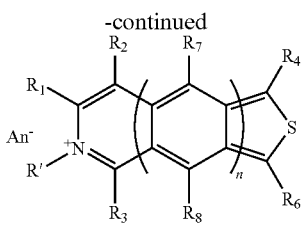

(Thiophene Derivative 3)

In the case of a thiophene derivative, a 2,3,4,5-tetraphenylthiophene derivative which is a non-condensed type compound and represented by the following general formula can also be used.

Formula 19

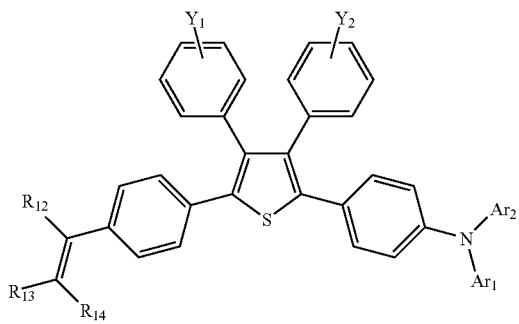

(wherein, $R_{12}$, $R_{13}$ and $R_{14}$ represent each independently a hydrogen atom, linear-, branched- or cyclic-alkyl group, substituted or unsubstituted aryl group, or substituted or unsubstituted aralkyl group, $Ar_1$ and $Ar_2$ represent a substituted or unsubstituted aryl group, further, $Ar_1$ and $Ar_2$ may form a nitrogen-containing heterocyclic ring together with a bonded nitrogen atom. $Y_1$ and $Y_2$ represent a hydrogen atom, halogen atom, linear-, branched- or cyclic-alkyl group, linear-, branched- or cyclic-alkoxy group, substituted or unsubstituted aryl group, substituted or unsubstituted aralkyl group, or substituted or unsubstituted amino group.)

(Thiophene Derivative 4)

A 2,3,4,5-tetraphenylthiophene derivative of the following general formula can also be used.

Formula 20

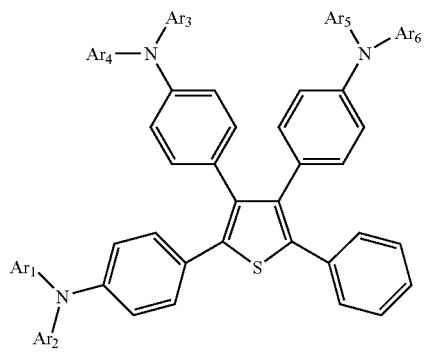

(wherein, $Ar_1$ to $Ar_6$ represent each independently a substituted or unsubstsituted aryl group, further, $Ar_1$ and $Ar_2$, $Ar_3$ and $Ar_4$, and $Ar_5$ and $Ar_6$ may form a nitrogen-containing heterocyclic ring together with a bonded nitrogen atom.)

Further, an imidazole can also be used as the 5-membered ring compound, for example, imidazole derivatives of the following general formulae.

(Imidazole Derivative 1)

Formula 21

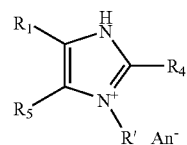

(Imidazole Derivative 2)

Formula 22

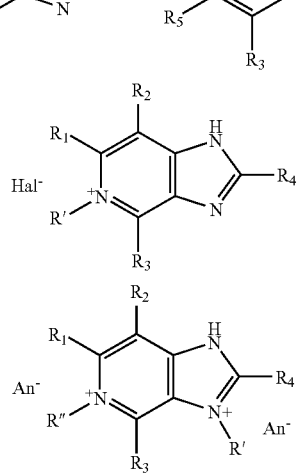

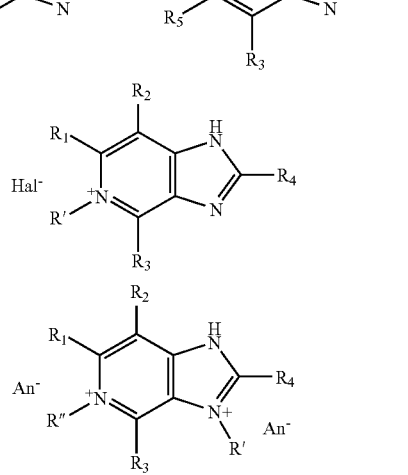

(Imidazole Derivative 3)

Formula 23

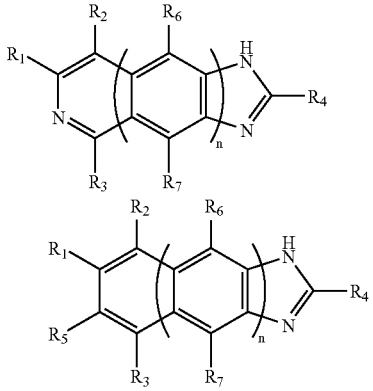

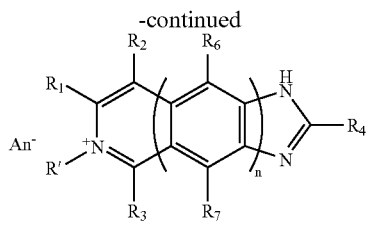
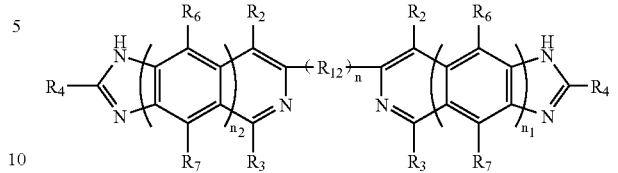
Formula 24-2
Formula 24-1
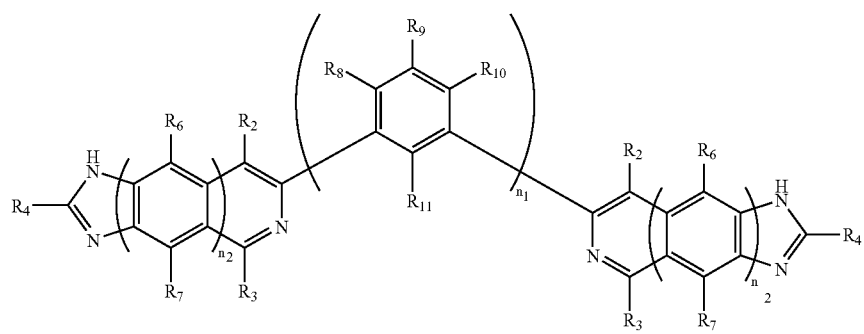
$n_1 = 1–5, n_2 = 0–5$
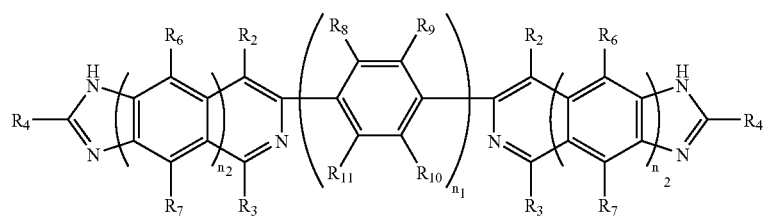
$n_1 = 1–5, n_2 = 0–5$
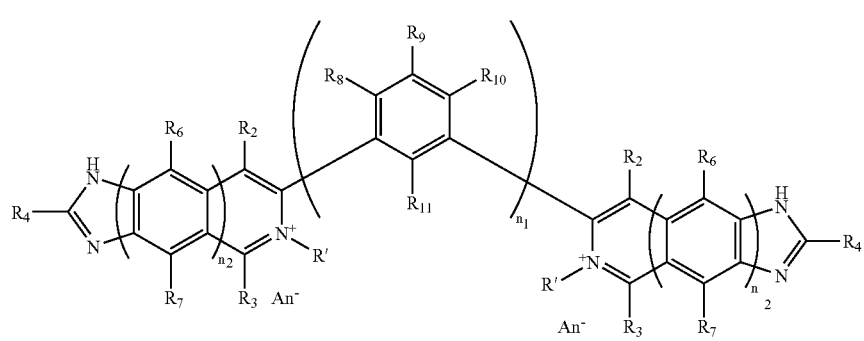
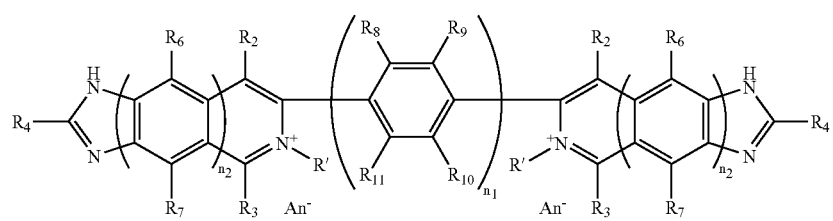

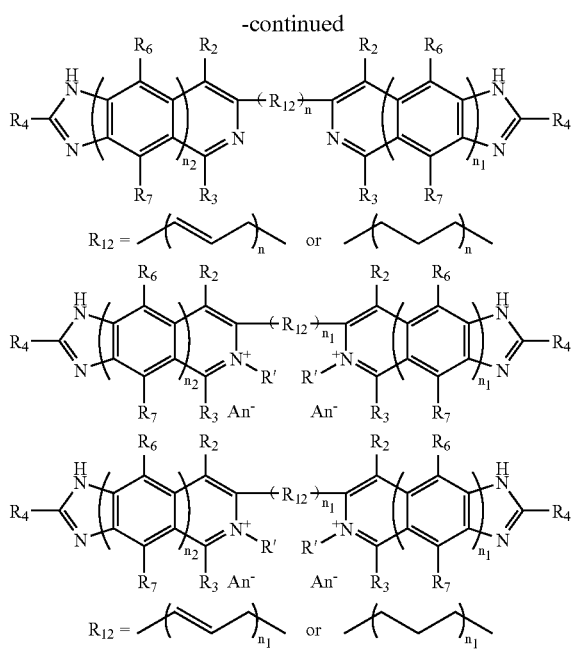

(wherein, in the imidazole skeleton, a plurality of units may be bonded to any position of center benzene rings $R_8$, $R_9$, $R_{10}$ and $R_{11}$, $R_{12}$ is an olefin group or paraffin group optionally having a substituent, and n represents an integer of 1 to 3, preferably 1.).

(Carbazole Derivative)

A carbazole derivative of the following general formula can also be used.

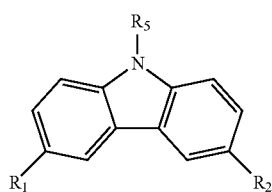

Formula 25

Further, a 5-membered ring compound which is a mono-ring compound having a conjugate system and containing one or more hetero atom(s), selenium atom(s) or boron atom(s) can also be used. Though not particularly limited, azole derivatives of the following general formula, for example, can also be used.

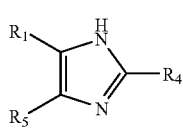

Formula 26

(wherein, $R_1$, $R_4$ and $R_5$ represent each independently an aromatic hydrocarbon group, hydrocarbon group, hetero-cyclic group or aromatic group containing a hetero atom in the ring, optionally having a substituent such as a hydrogen atom, halogen atom, hydroxyl group, cyano group or sulfonyl group and the like. $R_1$, $R_4$ and $R_5$ may be the same or different.)

The detection method of the present invention can be applied to any method for detection of a biomolecule provided it is a method of measuring the fluorescence of a labeled biomolecule in solid or semi-solid state. By using an organic EL-dye instead of a conventional fluorescence dye, a detection method that provides high sensitivity, chemical stability and excellent handling property as well as low costs can be provided. In the present invention, the biomolecule sample can be labeled with an organic EL-dye by directly reacting the biomolecule sample with an organic EL-dye as mentioned above. Alternatively, a method for labeling a biomolecule sample with an organic EL-dye by reacting a biomolecule sample and a probe labeled with an organic EL-dye can be used. Furthermore, a method comprising size separating a biomolecule sample labeled with an organic EL-dye by electrophoresis can be used.

For example, detection of a nucleic acid using DNA microarray method can be conducted according to the following procedure.

(DNA Micro-Array Method)

In this detection method, the fluorescence of the target nucleic acid is measured by reacting an organic EL-dye with a target nucleic acid to be detected to label the nucleic acid with the organic EL-dye while preparing a probe nucleic acid modified to be a single strand having a base sequence complementary to the target nucleic acid, and hybridizing the target nucleic acid modified to be a single strand and the probe nucleic acid on a substrate. In this detection method, in the case of investigation of a gene expression, a probe nucleic acid prepared by amplifying cDNA, etc. by PCR method using a cDNA library, genome library or whole genome as a template can be used as a probe nucleic acid to be fixed on a substrate. In the case of investigation of a gene mutation, etc., various oligonucleotides corresponding to mutation, etc. those synthesized based on a known sequence as a standard can be used.

A probe nucleic acid can be fixed on a substrate by a suitable method selected depending on the kinds of nucleic acid and substrate. For example, a method in which a probe nucleic acid is electrostatically bound to a substrate whose surface has been treated with cation such as polylysine, etc. utilizing charge of the DNA, can also be used. On the other hand, a target nucleic acid labeled with an organic EL-dye is prepared by mixing a target nucleic acid modified to be a single strand and an organic EL-dye and reacting them. The reaction temperature is preferably from room temperature to 60° C., and the reaction time is preferably from 2 to 48 hours.

Then, the labeled target nucleic acid is spotted on a substrate and hybridized. Hybridization is preferably conducted at room temperature to 70° C. for 2 to 48 hours. By hybridization, a target nucleic acid having a base sequence complementary to a probe nucleic acid is selectively bound to a probe nucleic acid. Thereafter, the substrate is washed and dried at room temperature. The fluorescence intensity of the surface of the dried substrate is then measured by fluorescence laser scanner method. The level of gene expression can be monitored by fluorescence intensity. Although the above-mentioned hybridization is explained based on a method of fixing a probe nucleic acid on a substrate, a method comprising fixing a target nucleic acid that has been labeled with an organic EL-dye in advance on a substrate and spotting a probe nucleic acid on the substrate can also be used.

Similarly, PCR method using a primer and a terminator, which also aims at detecting a nucleic acid, can be carried out by the following procedure.

(PCR Method)

In this detection method, the fluorescence of the target nucleic acid is measured by labeling a probe complementary to the base sequence of the target nucleic acid to be detected with an organic EL-dye, and reacting the target nucleic acid and the probe prior to or after the amplification of the target nucleic acid. Specifically, extension reaction of the target nucleic acid is carried out using an enzyme (DNA polymerase or RNA polymerase). During this reaction, the enzyme recognizes a double stranded nucleic acid sequence formed by the target nucleic acid and a primer comprising an oligonucleotide, and extension reaction is initiated from the recognized position, whereby only the objective gene region is amplified. The synthesis is carried out by the enzyme using a nucleotide (dNTP or NTP) as a raw material. During this reaction, by mixing a nucleotide comprising a dye as shown in FIG. 27 with a general nucleotide (dNTP or NTP) at an arbitral ratio, a nucleic acid in which the dye has been introduced by that ratio can be synthesized. Alternatively, a nucleic acid in which an organic EL-dye has been introduced can be synthesized by introducing a nucleotide having an amino group in an arbitral ratio and binding the organic EL-dye using PCR.

Formula 27

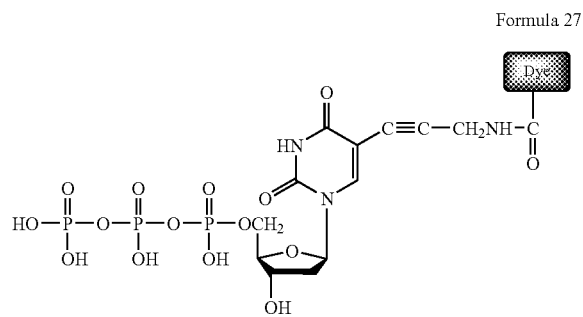

The synthesis by an enzyme is carried out using a nucleotide as a raw material. When a nucleotide in which the OH at 3' position has been substituted with H is used, extension reaction of the nucleic acid does not proceed any more, and at which time the reaction is completed. This nucleotide, dideoxynucleotide triphosphate (ddNTP), is referred to as a terminator. Where the nucleic acid is synthesized by mixing a general nucleotide with a terminator, the terminator is introduced at a constant probability. Therefore, when the reaction is completed, nucleic acids having various lengths are synthesized. These nucleic acids are subjected to size separation by gel electrophoresis, whereby DNAs are aligned in the sequence of length. Where the nucleic acids are labeled with different organic EL-dyes according to the kind of the base in the terminator in advance, a tendency dependent on each base is observed at the end point (3' end) of the synthesis reaction, and the base sequence information of the target nucleic acid can be obtained by reading fluorescence information beginning with the organic EL-dye labeled to the terminator. Alternatively, the nucleic acids can be hybridized to the target nucleic acid using a primer that has been labeled with an organic EL-dye in advance, instead of a terminator.

Alternatively, PNA (peptide nucleic acid) can be used as a probe. PNA is a nucleic acid in which a pentose-phosphoric acid skeleton, which is a basic skeleton structure of a nucleic acid, has been substituted with a polyamide skeleton comprising glycine as a unit, which has a three-dimension structure very similar to that of a nucleic acid, and binds very specifically and strongly to a nucleic acid having a complementary base sequence. Therefore, it is effective as a probe for detection of a specific nucleic acid. Accordingly, PNA can be used for not only existing DNA analysis methods such as in-situ hybridization method, etc. but also a reagent for research of a telomere by applying PNA to a telomere PNA probe.

For example, the detection can be carried out by contacting a double strand DNA with a PNA having base sequence(s) complementary to all or a part of the base sequence of DNA and having been labeled with an organic EL-dye to hybridize, heating the mixture to form a single strand DNA, cooling slowly the mixture to room temperature to prepare a PNA-DNA conjugate, and measuring its fluorescence.

In the above-mentioned case, a method for measuring fluorescence of the product by amplifying the target nucleic acid by PCR method can be used. However, in this method, the amount of the amplified product should be measured by determining the size of the product by electrophoresis and measuring the fluorescence intensity. Alternatively, the amount of the product can be measured in real time using a probe that is designed to generate fluorescence by utilizing energy transfer of the fluorescence dye to hybridize with the product of the PCR method. For this method, for example, a DNA labeled with a donor and an acceptor can be used. Examples of specific detection method may include molecular beacon method in which the existence of a nucleic acid having a specific sequence is detected, TaqMan-PCR method, cycling probe method, etc.

Figure 11:
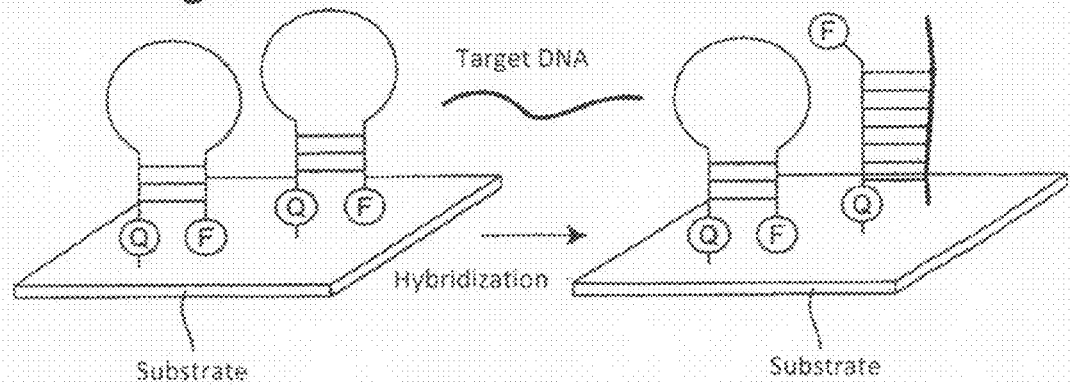
FIG. 11 is a schematic diagram showing a luminescence mechanism in a detection method of the present invention when a molecular beacon is used as a probe.

For example, the luminescence mechanism of the molecular beacon method in which a molecular beacon is fixed on a substrate and hybridized with the object gene is explained with referring to FIG. 11. An organic EL-dye F is labeled on one end of a DNA (probe) having a specific DNA sequence and quencher Q is labeled on another end of the DNA. The quencher Q has been fixed on the substrate. Before the objective gene is introduced, the quencher Q and the organic EL-dye F are close to one another, and the fluorescence dye is quenched. When an object gene having a sequence complementary to the labeled DNA is introduced, the labeled DNA and the object gene are hybridized, whereby the distance between the organic EL-dye F and the quencher Q increases and the fluorescence of the organic EL-dye F can be observed. As a result, hybridization of DNA can be observed and the amount of hybridization can be measured.

Where the object to be detected is a protein, a chromatic dye is used for the detection of the protein after electrophoresis. Generally, a method comprising penetrating a chromatic dye such as Coomassie Brilliant Blue (CBB) to a gel after electrophoresis to stain a protein and irradiating the protein with UV to cause luminescence is used. Although such method using a conventional chromatic dye is convenient, it is not suitable for the detection of trace protein because the sensitivity is low as about 100 ng. Furthermore, the method also has a problem in that long time is required for dying because the chromatic dye is penetrated through the gel.

On the other hand, in the present invention, a protein is subjected to size separation by electrophoresis, and an organic EL-dye binds to the separated protein to label the protein. The organic EL-dye used for the present invention is suitable for the detection of trace protein, because it has a reactive group, reacts with a protein quickly and quantitatively and has high sensitivity. Furthermore, the protein separated by size separation can also be identified by mass analysis.

Examples of the protein that can be detected include simple proteins such as albumin, globulin, glutelin, histone, protamine, collagen, etc., and conjugated proteins such as nucleus protein, glycoprotein, riboprotein, phosphoprotein, metal protein, etc. For example, phosphoprotein, glycoprotein and whole protein can be stained in a protein sample separated by two-dimensional electrophoresis using three organic EL-dyes that correspond to chromatic dyes for phosphoprotein, glycoprotein and whole protein. Furthermore, since the protein can be identified by mass analysis such as TOF-Mass, etc., it can be applied to the diagnosis or treatment of diseases that produce specific protein such as cancer, infectious diseases due to virus, etc. Collagen is a protein that constitutes binding tissues of animals, and has a unique fibrous structure, i.e., a structure having three polypeptide strands in which said peptide strands aggregate to form a triple strand. Generally, collagen is a protein having quite low immunogenicity, and is widely used in the fields of foods, cosmetics, pharmaceuticals, etc. However, where a fluorescence dye is introduced in the peptide strand of collagen, its stability is insufficient where a conventional fluorescence dye is used. Therefore, a more stable fluorescence dye is required. Accordingly, stable and high sensitivity detection can be carried out by using an organic EL-dye as a fluorescence dye for labeling collagen.

Figure 12:
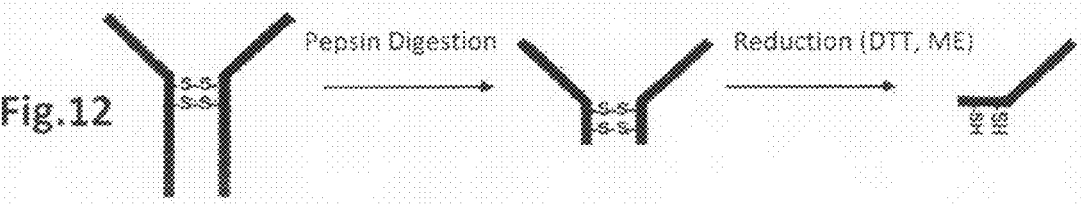
FIG. 12 is a schematic diagram showing a preparation method of F(ab') fragment of an InG antibody in a detection method of the present invention.
Figure 13:
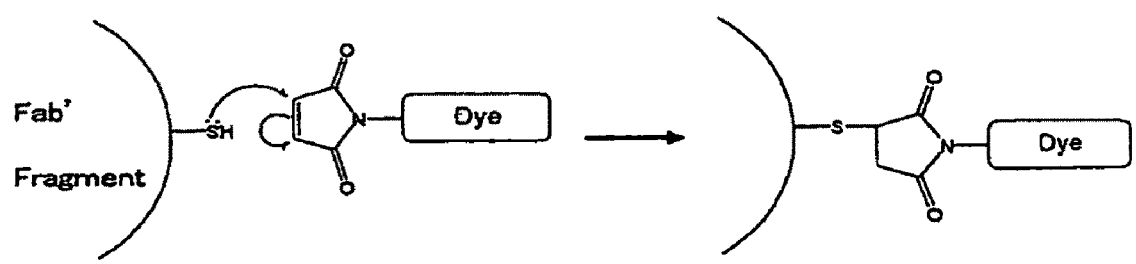
FIG. 13 is a schematic diagram showing a method for introducing an organic EL-dye to F(ab') fragment of an InG antibody in a detection method of the present invention.

Alternatively, the protein can be labeled by labeling an antibody that specifically binds to a protein with an organic EL-dye. For example, as shown in FIG. 12, a fragment that referred to as F (ab')$_2$ can be obtained by treating an IgG antibody with pepsin. The fragment is reduced using dithiothreitol, etc. to give a fragment that referred to as Fab'. The Fab' fragment has one or two thiol group(s) (—SH). Specific reaction can be carried out by reacting the thiol group(s) with maleimide group(s). Namely, as shown in FIG. 13, an antibody can be labeled with an organic EL-dye by reacting the organic EL-dye in which maleimide group(s) have been introduced with thiol group(s) of a fragment. In this case, the physiological activity (antibody capturing ability) of the antibody is not deteriorated.

Meanwhile, an aptamer that specifically binds to a specific biomolecule (specifically protein) can be used as a probe for the detection method of the present invention. Since the aptamer comprises an oligonucleic acid and can form various characteristic stereo structures depending on the base sequence, it can bind to many biomolecules including proteins via its stereo structure. Using this characteristic, the object substance can be detected by binding an aptamer labeled with an organic EL-dye to a specific protein, and detecting indirectly the object substance to be detected from the variation of fluorescence according to the change of the structure of the protein due to binding to the object substance to be detected. For example, a biosensor for detecting cocaine using an aptamer labeled with a fluorescence dye and utilizing energy transfer has been suggested (J. Am. Chem. Soc. 2001, 123, 4928-4931). By using an organic EL-dye instead of the above-mentioned fluorescence dye, a biosensor that provides high sensitivity and easy handling property can be provided.

Alternatively, metal ion can be detected using the detection method of the present invention. Metal ion participates to every life phenomena that occur in a living body, such as maintenance of stability and high dimension structure of DNAs, proteins, etc. in a body, expression of functions, activation of enzymes that control all chemical reactions in a living body, etc. Therefore, importance of a metal ion sensor, which can observe behavior of metal ion in a living body in real time, is growing in the field of medical. Conventionally, a metal ion sensor in which a fluorescence dye has been introduced in a biomolecule is known. For example, a metal ion sensor that utilizes a nucleic acid having a sequence that forms a specific structure by incorporating $K^+$ ion in the presence of $K^+$ ion has been suggested (J. AM. CHEM. SOC. 2002, 124, 14286-14287). A fluorescence dye that initiates energy transfer is introduced in both ends of a nucleic acid. Generally, energy transfer does not occur due to distance between the dyes. However, in the presence of $K^+$ ion, the nucleic acid forms a specific shape, whereby the fluorescence dyes verge in a distance that occurs energy transfer and fluorescence can be observed. In addition, a zinc ion sensor in which a fluorescence dye has been introduced in a peptide has been suggested (J. Am. Chem. Soc. 1996, 118, 3053-3054). By using a label dye comprising an organic EL-dye of the present invention instead of these conventional fluorescence dyes, a metal ion sensor that provides high sensitivity and easy handling property can be provided. All kinds of metal ion existing in a living body can be detected.

Moreover, intercellular signal can be observed using the detection method of the present invention. For the response of cells to internal signal or environmental information, various molecules from ions to enzymes are participated. It is known that in the process of signal transmission, a specific protein kinase is activated and induces phosphoration of a specific cell protein, which bears initial response for various cell responses. Binding and hydrolysis of nucleotides play an important role in these activities, and signal transmission behavior can be readily observed using a nucleotide derivative. For example, protein kinase C (PKC) plays an important role for signal transmission in a cell membrane. This $Ca^{2+}$ dependant serine/threonine protein kinase is activated on a membrane-constituting lipid such as diacylglycerol, phosphatidyl serine, etc., which phosphorizes serine and threonine existing on an ion channel and a cell skeleton protein to vary electron charge on the membrane surface, whereby signal transmission is achieved. By dynamically observing these phenomena in living cells, signal transmission of the cells can be observed.

In this observation, the nucleotide derivative is provided as a substrate or an inhibitor for an enzyme, and it is used for search for the structure and dynamics of a lone protein and reconstruction of a membrane binding protein enzyme, and binds to organelle such as mitochondria, nucleotide-binding protein portion of tissues such as skinned muscle fiber so as to control them. Furthermore, existence of compounds that affect signal transmission such as inhibitors or active forms for G-protein has been recently revealed. By introducing the labeled dye including the organic EL-dye of the present invention into this nucleotide derivative, dynamic observation of the intercellular signal transmission thereof can be carried out at high sensitivity and with easy handling.

Alternatively, the detection method of the present invention can be used for the observation of gene expression utilizing RNA interference (RNAi). RNAi is a phenomenon where RNA is introduced into a cell, the expression of gene having the same sequence as said RNA is knocked down. The RNAi decompose mRNA of the target gene by introducing a double strand RNA (dsRNA) into a cell and suppresses expression. In this process, a long chain dsRNA (double stranded RNA) is firstly cleaved into a short chain siRNAs having 21 to 23 mers by Dicer having ribonuclease activity. It is known that the generated siRNAs are uptaken by an intermediate conjugate (RNA-induced silencing complex (RISC)), whereby mRNAs having sequences complementary to the antisense chains of the siRNAs uptaken by this conjugate are cleaved. Also in this field, a fluorescence dye is used for observing gene expression state, etc. Using an organic EL-dye as a fluorescence dye for labeling, stable and high sensitivity detection can be carried out.

The labeling kit of the present invention contains an organic EL-dye or derivative thereof for labeling a biomolecule, and if necessary, it can contain reagents, enzymes, solvents, etc., for reacting a dye with the object biomolecule. The object biomolecules include nucleic acids, proteins, peptides or saccharides. The organic EL-dye is preferably a derivative having a functional group that reacts with an amino group of a biomolecule. Examples of the functional group preferably include any one selected from an isocyanate group, an isothiocyanate group, an epoxy group, a halogenated alkyl group, a triazine group, a carbodiimide group and an active-esterified carbonyl group. Further preferably, an active ester containing a triazine group, a carbodiimide group or an active-esterified carbonyl group is contained as a derivative of an organic EL-dye.

The labeled dye of the present invention can also be used as a chromatic dye for tissues or cells used for determination of the expression level of the target nucleic acid or target protein in a tissue sample or a cell sample. The tissues or cells can be stained by binding an organic EL-dye with a target nucleic acid or a target protein via reactive groups as mentioned above.

Accordingly, the chromatic dye of the present invention shows superior performance than conventional dyes in view of storage after labeling, since the organic EL-dye generates fluorescence even in dry state when it is used, for example, for staining of eucaryotic cells. Furthermore, it can also be sufficiently used as a dye for cell skeletons as well as a dye for eucaryotic cells. Moreover, it can be used for labeling of mitochondria, Golgi body, endoplasmic reticulum, lysosome, lipid double membrane, etc. These labeled cells, etc. can be observed under all wet or dry conditions, and thus have great versatility. A fluorescence microscope, etc. can be used for observation.

Generally, tissues collected from human bodies during clinical stage are sliced using an instrument such as a microtome, etc. in thin slices and stained. In this case, Cy dye and Alexa dye are used. However, since the existing dyes have poor stability, it is necessary to prepare samples again in the next diagnosis. Furthermore, the samples prepared cannot be stored in the form of a specimen. On the other hand, the organic EL-dye is a very stable dye as compared to the above-mentioned conventional dyes. Therefore, the stained tissues can be stored in the form of a specimen.

The present invention will be further specifically explained in more detail in the following examples.

SYNTHESIS EXAMPLE 1

A 1,2,5-oxadiazolo-[3,4-c]pyridine derivative was used as the organic EL-dye.

The scheme for synthesis of an active ester of a 1,2,5-oxadiazolo-[3,4-c]pyridine (hereinafter, abbreviated as EL-OSu) will be shown below.

Scheme 3

Formula 28

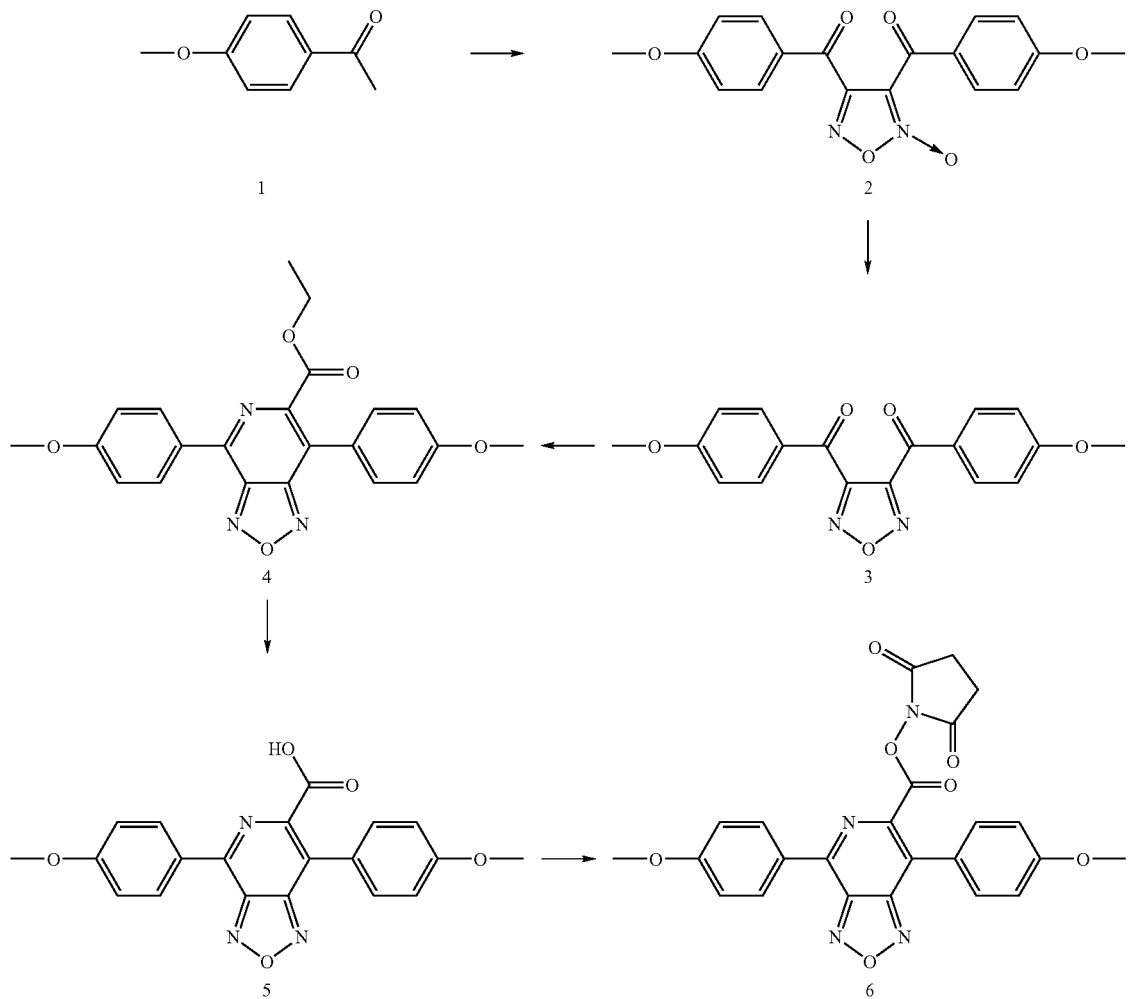

(1) Synthesis of Diketone Derivative (2)

In a 500 mL three-necked flask, 37.5 g (0.25 mol) of 4-methoxyacetophenone (1) and 0.15 g of sodium nitrite were dissolved in 100 mL of acetic acid. On a water bath, a solution prepared by dissolving 100 mL of $HNO_3$ in 100 mL of acetic acid was added dropwise over 2 hours. Then, the mixture was stirred at room temperature for 2 days. The reaction mixture was slowly added into 500 mL of water to cause precipitation. The precipitate was filtrated and dissolved in chloroform. The chloroform phase was washed with saturated sodium bicarbonate water, and washed twice with a 10% NaCl aqueous solution. After dehydration over $MgSO_4$, chloroform was distilled off under reduced pressure to obtain 34.5 g (yield: 78%) of oxadiazole-N-oxide (2).

(2) Synthesis of Diketone Derivative (3)

In a 500 mL three-necked flask, 17.7 g (0.05 mol) of oxadiazole-N-oxide (2) was dissolved in 400 mL of acetonitrile. Into this was added 12.0 g of Zn, 7 mL of AcOH and 20 mL of $Ac_2O$. On a water bath, the resulted mixture was cooled so that the reaction temperature did not exceed 30° C. The mixture was stirred for 12 hours to terminate the reaction. The reaction mixture was filtrated to remove insoluble materials. Acetonitrile was distilled off under reduced pressure to obtain a residue. The residue was recrystallized from chloroform to obtain 10.2 g (yield: 60%) of oxadiazole-N-oxide (3).

(3) Synthesis of Oxadiazolopyridine Ethyl Ester (4)

In a 500 mL three-necked flask, 15.6 g (0.046 mol) of oxadiazole-N-oxide (3) was dissolved in 300 mL of butanol. Into this was added 32.0 g (0.23 mol) of a glycine ethyl ester hydrochloride. The mixture was heated to reflux for 24 hours. Butanol was distilled off under reduced pressure to obtain a residue. The residue was dissolved in 200 mL of chloroform, and washed with 10% HCl, saturated $NaHCO_3$ and 10% NaCl. This was dried over $MgSO_4$ and the solvent was distilled off. The resulted residue was recrystallized from chloroform to obtain 13.0 g (yield: 70%) of oxadiazolopyridine ethyl ester (4).

(4) Hydrolysis of Oxadiazolopyridine Ethyl Ester (4)

In a 500 mL three-necked flask, 3.0 g (0.007 mol) of oxadiazolopyridine ethyl ester (4) was dissolved in 200 mL of ethanol. To this was added 0.62 g (0.01 mol) of KOH. After heating to reflux for 5 hours, the reaction mixture was added to 200 mL of water. Into this aqueous solution, concentrated hydrochloric acid was added dropwise to adjust pH to 1 to obtain a precipitate. The precipitate was filtrated and dissolved in chloroform. The chloroform phase was washed with a 10% $NaHCO_3$ aqueous solution and water. Chloroform was distilled off to obtain a residue. The residue was recrystallized from water-ethanol (1:1) to obtain 2.1 g (yield: 81%) of oxadiazolopyridinecarboxylic acid (5)

Synthesis of Active Ester (6)

In a 50 mL three-necked flask, 1.0 g (0.0026 mol) of oxadiazolopyridinecarboxylic acid (5) and 0.30 g (0.0026 mol) of N-hydroxysuccinimide were dissolved in 20 mL of DMF. Into this, 0.54 g (0.0026 mol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.76 g (yield: 62%) of an oxadiazolopyridine active ester (6).

SYNTHESIS EXAMPLE 2

An imidazolopyridine ethyl ester derivative was used as a organic EL-dye. The scheme for synthesis of an active ester of a imidazolopyridine ethyl ester (hereinafter, abbreviated as im-EL-OSu) will be shown below.

Scheme 4

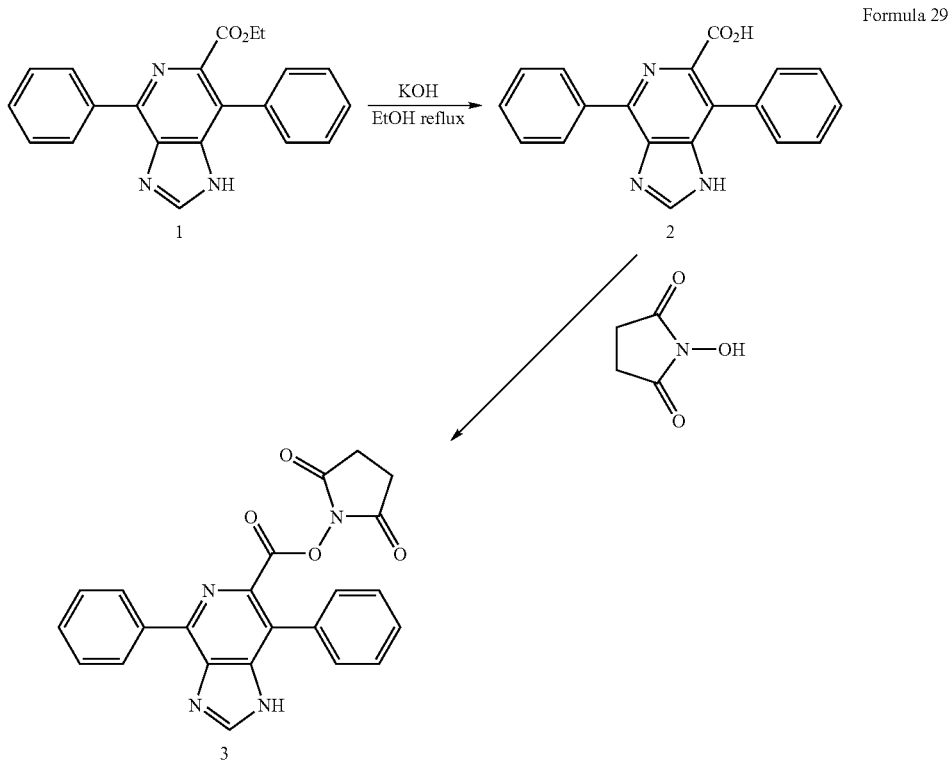

Formula 29

(1) Hydrolysis of Imidazolopyridine Ethyl Ester (1)

In a 500 mL three-necked flask, 0.5 g (1.5 mmol) of an ester 1 was dissolved in 50 mL of ethanol. To this was added 0.12 g (2.1 mol) of KOH. After heating to reflux for 5 hours, the reaction mixture was added to 50 mL of water. Into this aqueous solution, concentrated hydrochloric acid was added dropwise to adjust pH to 1 to obtain a precipitate. The precipitate was filtrated and dissolved in chloroform. The chloroform phase was washed with a 10% $NaHCO_3$ aqueous solution and water. Chloroform was distilled off to obtain a residue. The residue was recrystallized from water to obtain 0.3 g (yield: 63%) of a carboxylic acid 2.

(2) Synthesis of Active Ester (3)

In a 50 mL three-necked flask, 0.2 g (0.6 mmol) of a carboxylic acid derivative 2 and 0.07 g (0.6 mmol) of N-hydroxysuccinimide were dissolved in 10 mL of DMF. Into this, 0.12 g (0.6 mmol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.14 g (yield: 55%) of an active ester 3.

EXAMPLE 1

<Labeling of Oligonucleotide with Dye, and Detection Thereof (1)>

1. Labeling of Oligonucleotide with Dye

Labeling of an oligonucleotide with a dye was conducted according to the following Scheme 4.

Scheme 4.

Formula 30

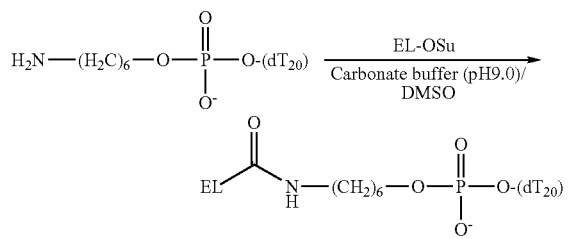

(Experimental Procedure)

Into 40 μl of $Na_2CO_3/NaHCO_3$ buffer (pH 9.0) containing $H_2N$-$dT_2O$ (40 mmol) was added 12 μl of an anhydrous DMSO solution containing 5.0 μmol (2.4 mg) of an active ester of an organic EL-dye and the mixture was shaken at room temperature for 6 hours. After shaking, 0.1 M TEAA (triethylamine acetic acid) buffer (pH 7.0) was added so as to give the total volume of 1 ml, and components derived from the oligonucleotide were separated using NAP-10 column (Pharmacia Sephadex G-25). In this operation, the NAP-10 column had been equilibrated previously with 15 ml of 0.1 M TEAA buffer before use. The sample solution of which total volume had been adjusted to 1 ml was applied into a column. After elution of 1 ml of the solution, 0.1 M TEAA buffer was charged in a volume of 1.5 ml. Immediately after this, 1.5 ml of the eluted solution was separated. The resulted solution was freeze-dried over night, and 20 μl of sterile distilled water was added and analyzed by reverse phase HPLC. The solution injected into HPLC was previously diluted to 1/40 and analyzed.

(HPLC Measurement Conditions)

Column: Lichrospher RP-18 (Cica-MERCK)
Flow rate: 1 ml/min
Detection wavelength: 260 nm
Sample injection solvent: ultra-pure water
Eluent A: 0.1 M TEAA buffer (pH 7.0), 10% $CH_3CN$ solution
Eluent B: 0.1 M TEAA buffer (pH 7.0), 40% $CH_3CN$ solution

TABLE 1

| Gradient conditions of HPLC measurement | | | | |
|---|---|---|---|---|
| | 0 | 30 | 35 | 40 (min) |
| A | 100 | 0 | 0 | 100 (%) |
| B | 0 | 100 | 100 | 0 (%) |

Figure 1B:
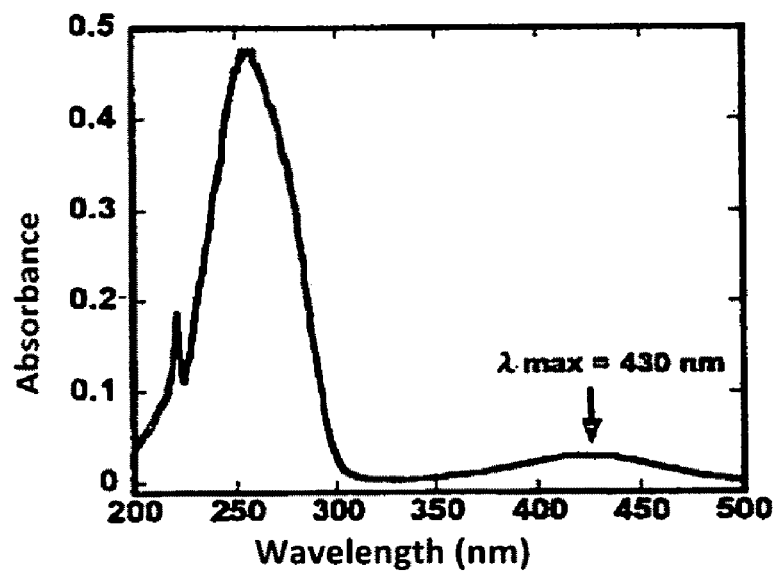
FIG. 1B shows one example of the UV spectrum of an intended labeled oligonucleotide in Example 1 of the present invention.
Figures 2, 3:
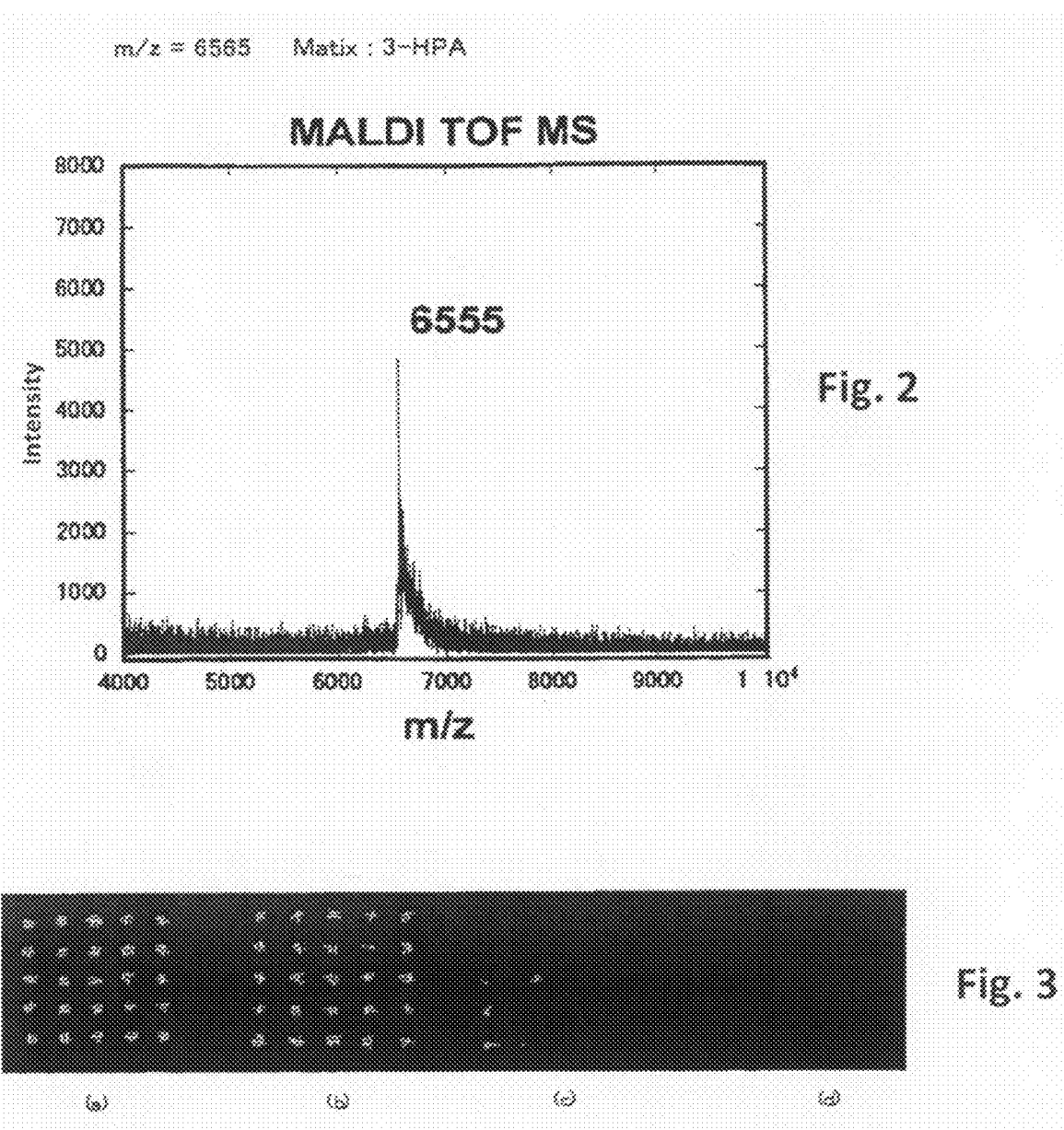
FIG. 2 shows one example of the TOF MS spectrum of a labeled oligonucleotide in Example 1 of the present invention.
FIG. 3 shows one example of the emission pattern of a labeled oligonucleotide in Example 1 of the present invention, and (a), (b), (c) and (d) show results of 110 fmol, 10 fmol, 1 fmol and 0.5 fmol, respectively.

The HPLC profile of the labeled oligonucleotide and the UV spectrum of the intended material are shown in FIG. 1A and FIG. 1B, respectively. As a result of HPLC, a peak around RT=30 min was confirmed to be the intended material, and preparative HPLC was conducted. Identification of the resulted intended material was conducted by MALDI (Matrix Assisted Laser Desorption/Ionization) TOF MS. The result is shown in FIG. 2. The reaction ratio was calculated from the peak area in HPLC chromatogram to find a ratio of about 90%, namely, the active ester (6) of an EL-dye was reacted almost quantitatively with oligo DNA.

2. Detection of Labeled Oligonucleotide

Next, solutions of different concentration of the labeled oligonucleotide were prepared as shown in the following Table 2. Then, 1 nL of the solution was spotted on a glass substrate (5×5). After spotting, the glass substrate was dried.

TABLE 2

| Solution concentration (μM) | Relative concentration of labeled oligonucleotide (fmol) |
|---|---|
| 110 | 110 |
| 11 | 11 |
| 1 | 1 |
| 0.5 | 0.5 |

Next, the detection limit thereof was investigated by a fluorescence scanner. The results are shown in Table 3. Here, (a), (b), (c) and (d) show results of 110 fmol, 10 fmol, 1 fmol and 0.5 fmol, respectively.

Here, as the detection instrument, BIO-RAD molecule imager FX Pro was used. The laser wavelength was 488 nm and the scan interval was 50 nm.

(Result)

The excitation light used in this detection is laser light of 488 nm and the excitation wavelength of the fluorescence dye is 438 nm. Irrespective of this, the detection limit of the relative concentration of the labeled oligonucleotide was 0.5 fmol (500 amol), and therefore, detection in high sensitivity was possible. The reaction with DNA was almost quantitative, and the reaction time could be reduced from conventional times of about 24 hours to about 6 hours. Further, this EL-dye was stable, and even when re-measurement was conducted using an EL-dye preserved at room temperature for 15 days, the equivalent results were obtained.

EXAMPLE 2

<Labeling of Oligonucleotide with Dye, and Detection Thereof (2)>

1. Labeling of Oligonucleotide with Dye

Labeling of an oligonucleotide with a dye was conducted according to the following Scheme 4. The labeling conditions are the same as that for Example 1. The addition reaction of an imidazole derivative progressed quickly and almost quantitatively.

Scheme 5.

Formula 31

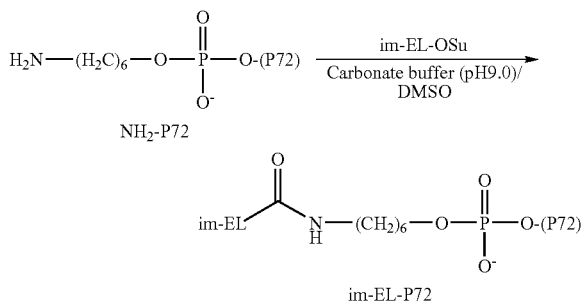

Figure 4A:
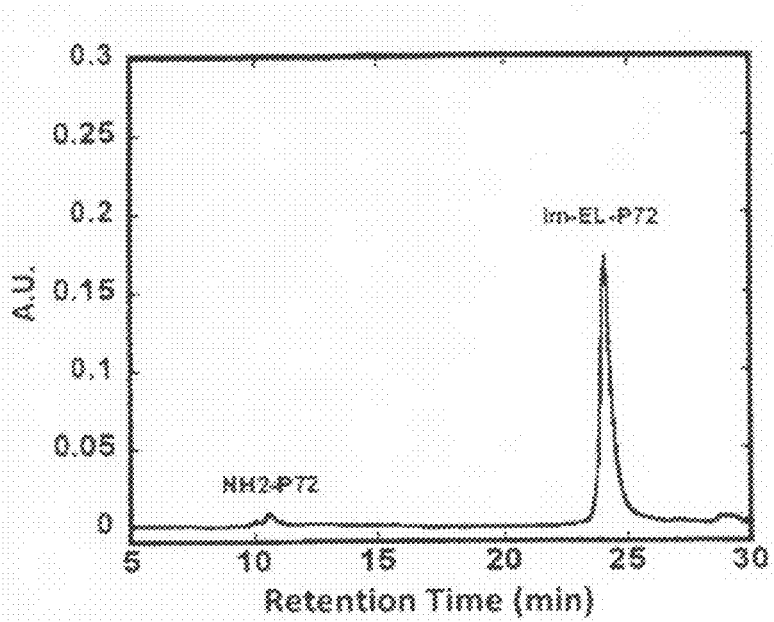
FIG. 4A shows one example of the HPLC profile of a labeled oligonucleotide in Example 2 of the present invention.
Figure 4B:
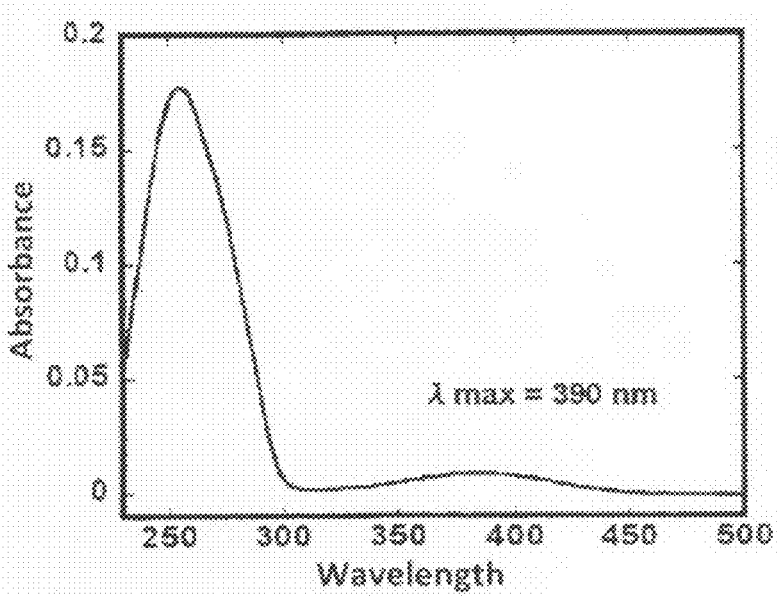
FIG. 4B shows one example of the UV spectrum of an intended labeled oligonucleotide in Example 2 of the present invention.

(HPLC Measurement Conditions)
Column: Lichrospher RP-18 (Cica-MERCK)
Flow rate: 1 ml/min
Detection wavelength: 260 nm
Sample injection solvent: ultra-pure water
Eluent A: 0.1 M TEAA buffer (pH 7.0), 10% $CH_3CN$ solution
Eluent B: 0.1 M TEAA buffer (pH 7.0), 40% $CH_3CN$ solution The gradient conditions of HPLC measurement are the same as that of Example 1. The HPLC profile of the labeled oligonucleotide and the UV spectrum of the intended material are shown in FIG. 4A and FIG. 4B, respectively. As a result of HPLC, a peak around RT=25 min was confirmed to be the intended material, and preparative HPLC was conducted.

Figure 5:
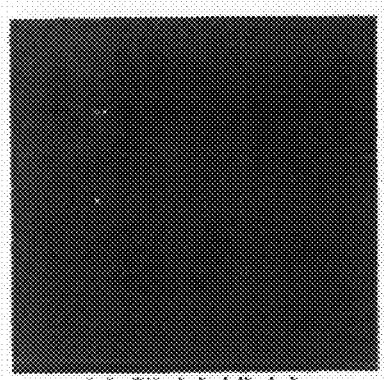
FIG. 5 shows one example of the emission pattern of a labeled oligonucleotide in Example 2 of the present invention, and (a), (b), (c), (d) and (e) show results of 500 fmol, 250 fmol, 100 fmol, 50 fmol and 10 fmol, respectively.

Next, the detection limit thereof was investigated by fluorescence scanner in the same manner as that of the example. The results are shown in FIG. 5. Here, (a), (b), (c), (d) and (e) show emission patterns of 500 fmol, 250 fmol, 100 fmol, 50 fmol and 10 fmol, respectively.

(Result)

The detection limit of the relative concentration of the labeled oligonucleotide was 10 fmol, and therefore, detection in high sensitivity was possible. The reaction of the oligonucleotide and EL-dye was almost quantitative.

EXAMPLE 3

<Labeling and Detection of Peptides>
1. Synthesis of Ac-Lys(EL)-Lys-Lys-Lys(Acr)-Lys-Lys-Lys(Acr)-Lys-Lys-$NH_2$
(1) Synthesis of Ac-Lys(Mtt)-(Lys(Boc))$_2$-Lys-(Acr)-(Lys(Boc))$_2$-Lys(Acr)-(Lys(Boc))$_2$-Resin
(where, Lys denotes lysine, Mtt denotes 4-methyltrityl, Boc denotes tert-butyloxycarbonyl, and Acr denotes acridinyl, respectively)

(Experimental Procedure)

Into a reaction vessel, 0.15 g (0.61 mmol/g) of Fmoc (9-fluorenylmethyloxycarbonyl)-NH— SAL (super acid labile) Resin was charged, and 0.26 g of Fmoc-Lys(Acr)-OH was added in each of cartridges 3, 6, 0.18 g of Fmoc-Lys (Boc)-OH was added in each of cartridges 1, 2, 4, 5, 7 and 8, and 0.23 g of Fmoc-Lys(Mtt)-OH was added in a cartridges 9. Subsequently, synthesis was conducted using 431A peptide synthesizer of Applied Biosystems. The standard Fmoc method was followed, and the N-terminal was acetylated. A yellow solid peptide resin was obtained. The yield was 0.30 g.

(2) Deprotection of Mtt Group of Ac-Lys(Mtt)-(Lys(Boc))$_2$-Lys-(Acr)-(Lys(Boc))$_2$-Lys(Acr)-(Lys(Boc))$_2$-Resin, and Modification by EL, cleavage from Resin, and Deproduction of Side Chain (Experimental Procedure)

i) Deprotection of Mtt Group

Into a screw tube, 0.30 g of the peptide resin synthesized in 1 was charged, and to this was added excess amount of dichloromethane (DCM) and swollen over 30 minutes, then excess DCM was removed by a nitrogen gas. Thereafter, 4 ml of a mixed solution of DCM:TFA (trifluoroacetic acid):TIPS (tri-isopropylsilane)=94:1:5 was added and the mixture was stirred for 2 minute, and the solvent was removed by a nitrogen gas. This operation was repeated five times, and suction filtration was conducted. The residue was washed with DCM, triethylamine and DCM, then dried under reduced pressure.

ii) Modification by Methoxy Type Organic EL-Dye

To the peptide resin dried under reduced pressure, 6 mL of 1-methyl-2-pyrrolidone (NMP) was added, and the mixture was stirred for 30 minute to swell, and 0.15 ml of triethylamine was added and the mixture was stirred. Further, 0.2 g of the active ester (6) was added and the mixture was stirred at room temperature for 24 hours. Then, suction filtration was conducted, and the residue was washed with NMP and DCM and dried under reduced pressure.

iii) Cleavage from Resin and Deproduction of Side Chain

To the peptide resin dried under reduced pressure, 0.08 ml of m-cresol, 0.48 ml of thioanisole and 3.44 ml of TFA were added, and the mixture was stirred at room temperature for 1 hour. Then, the mixture was suction-filtrated and washed with TFA. TFA was distilled off under reduced pressure, and in an ice bath, 15 ml of ether was added. After treatment by ultrasound, the mixture was left for a while, and the supernatant was removed. Then, in an ice bath, 15 ml of ethyl acetate was added. After ultrasound treatment, the mixture was left for a while. Then, the mixture was filtrated under reduced pressure and washed with ether, and dried under reduced pressure.

Figure 6A:
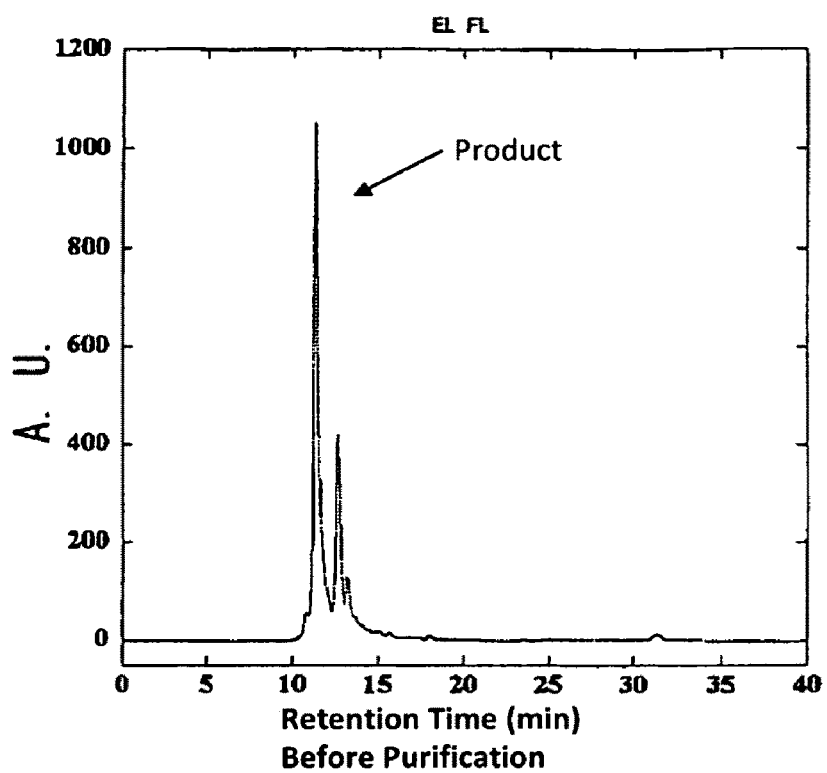
FIG. 6A shows one example of the HPLC profile of a labeled peptide in Example 3 of the present invention before purification.
Figure 6B:
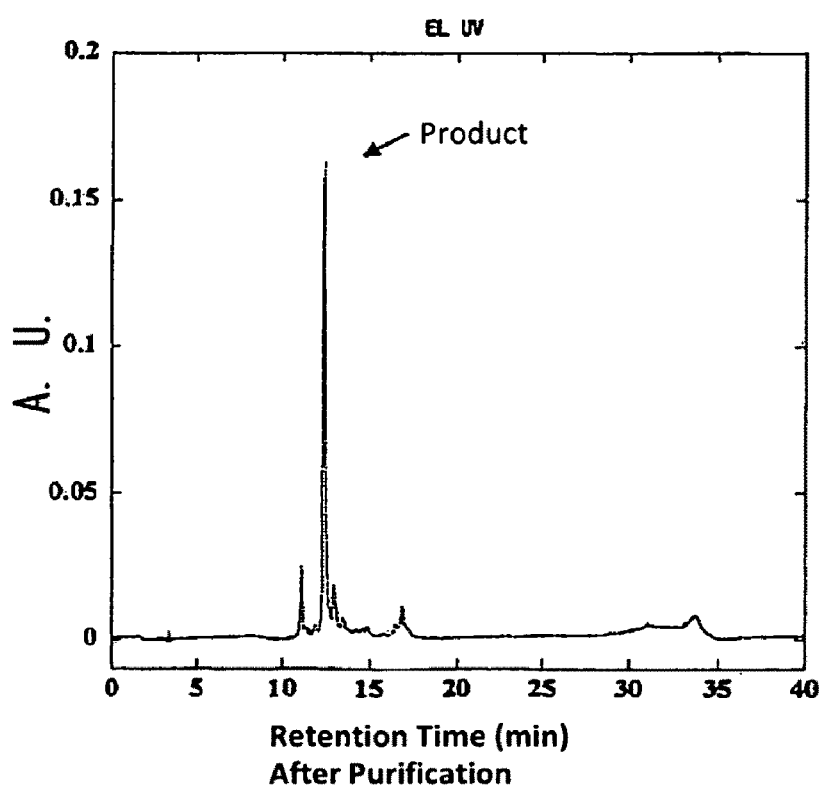
FIG. 6B shows one example of the HPLC profile of a labeled peptide in Example 3 of the present invention after purification.
Figure 7:
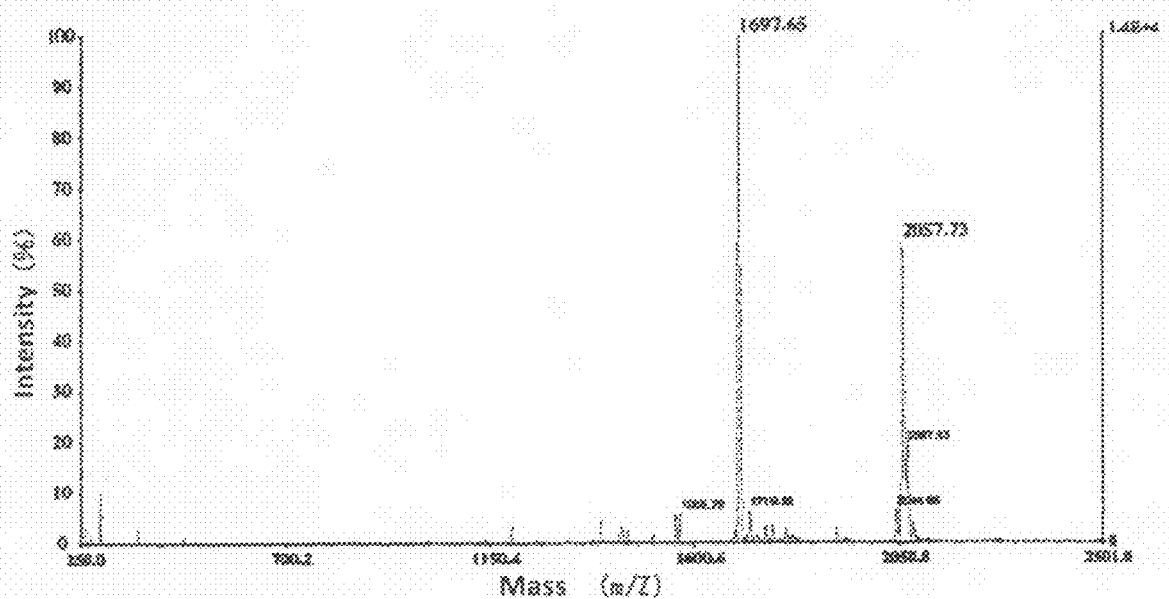
FIG. 7 shows one example of the TOF MS (Time of Flight Mass Spectrometry) spectrum of a labeled peptide in Example 3 of the present invention.

Orange color solid was obtained, and the yield was 0.29 g. HPLC prpfiles before purification and after purification of the product are shown in FIG. 6A and FIG. 6B, respectively. A sample showing a peak around R.T.=12.5 min was subjected to TOF-Mass measurement. As a result, a peak at 2057.33 was observed corresponding to a molecular weight of a complex of an EL-dye and peptide (EL-Peptide) of 2055.30, confirming the production of the intended material (Matrix: α-cyano-4-hydroxycinnamic acid (α-CHCA); FIG. 7)

2. Detection of Peptide

In the same manner as that of Example 1, a labeled peptide spotted on a glass substrate was detected. As the detection instrument, BIO-RAD molecule imager FX Pro was used. The laser wavelength was 488 nm and the scan interval was 50 nm.

(Result)

Figure 8:
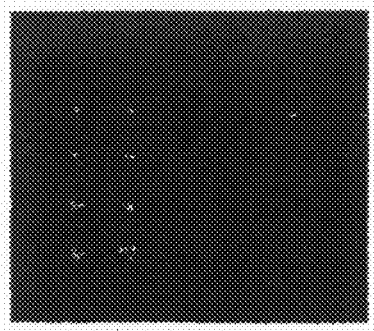
FIG. 8 shows one example of the emission pattern of a labeled peptide in Example 3 of the present invention, and (a), (b), (c), (d) and (e) show results of 10 fmol, 5 fmol, 1 fmol, 0.5 fmol and 0.1 fmol, respectively.

FIG. 8 shows an emission pattern of the labeled peptide, and (a), (b), (c), (d) and (e) show emission patterns of 10 fmol, 5 fmol, 1 fmol, 0.5 fmol and 0.1 fmol, respectively. The detection limit of the relative concentration of the labeled peptide was 0.1 fmol (100 amol), and therefore, detection in high sensitivity was possible. The reaction of the peptide and EL-dye was almost quantitative.

EXAMPLE 4

<Labeling of Proteins with Dye, and Detection Thereof>

1. Labeling of Protein with Dye

An amino group of a lysine residue of bovine serum albumin (BSA) and an active ester of an organic EL-dye were reacted to form an amide bond for labeling of BSA. Specifically, to 58 μl of carbonate buffer (pH 9.0) containing 4.0 mg (58 nmol) of BSA was added 40 μl of a DMSO solution containing 3.6 mg (8.6 μmol) of an active ester of an organic EL-dye (EL-OSu) and the mixture was shaken at 37° C. for 24 hours. 0.1 M TEAA buffer (pH 7.0) was added so as to give the total volume of 1 ml, and components derived from BSA were separated using NAP-10 column (Pharmacia Sephadex G-25), and the separated solution was freeze-dried over night.

Figure 9A:
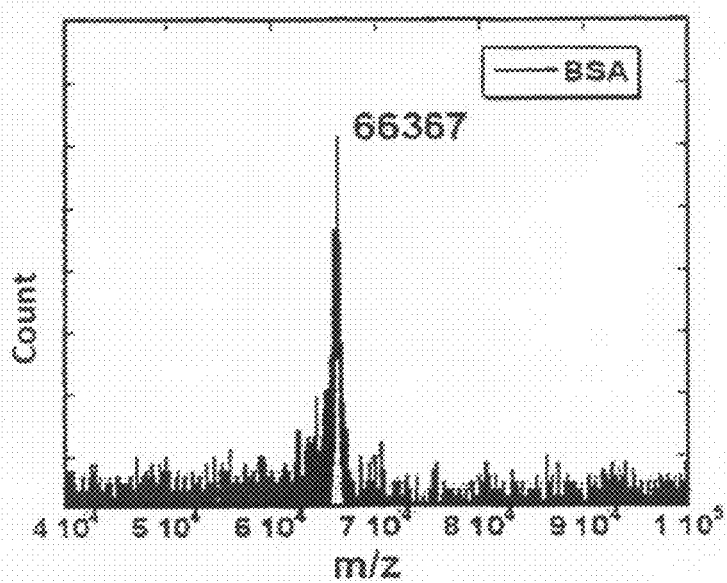
FIG. 9A shows one example of the TOF MS spectrum of a labeled protein in Example 4 of the present invention before labeling.
Figure 9B:
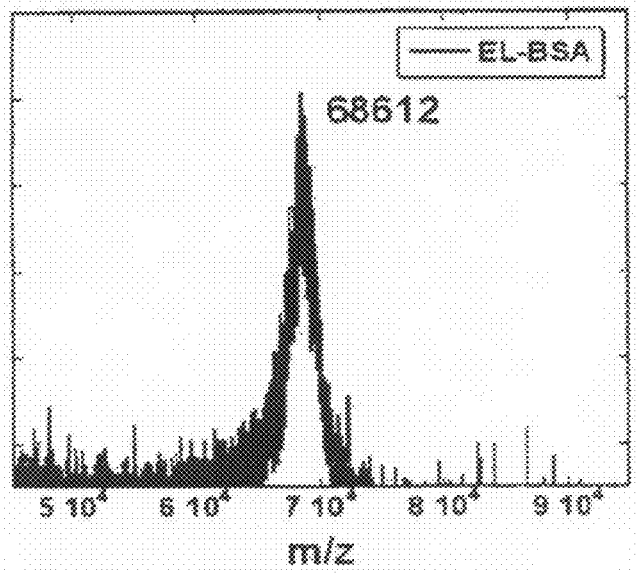
FIG. 9B shows one example of the TOF MS spectrum of a labeled protein in Example 4 of the present invention after labeling.

Identification of BSA labeled with an organic EL-dye was conducted by MALDI TOF MS. As shown in FIG. 9, the labeled BSA (FIG. 9B) had molecular weight increased by about 2200 as compared with the raw material (FIG. 9A), showing that about five organic EL-dyes was bonded thereto.

2. Detection of Protein (Result)

Figure 10:
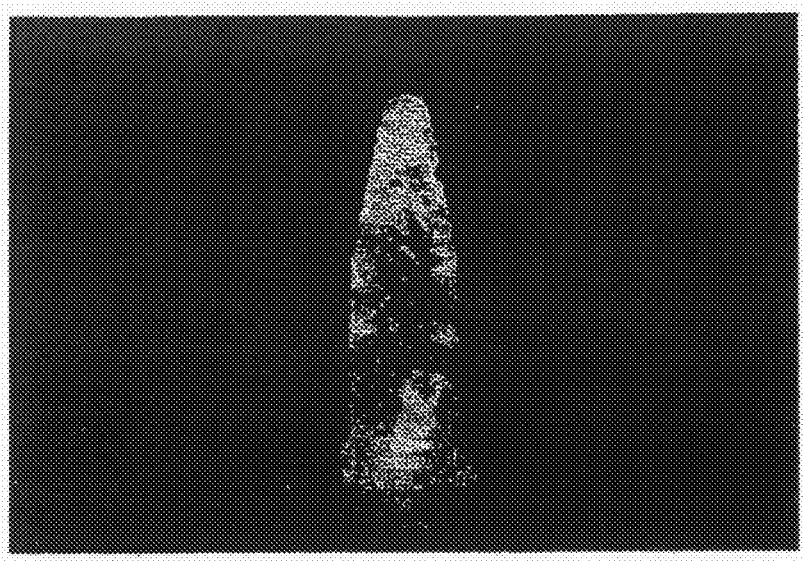
FIG. 10 shows one example of the emission pattern of a labeled protein in Example 4 of the present invention.

The prepared BSA emitted fluorescence in solid state as shown in FIG. 10. Thus, it was clarified that a protein can be labeled by an active ester of an organic EL-dye.

The invention claimed is:

1. A method of detecting a biomolecule, comprising reacting a biomolecule sample and a probe labeled with an organic EL-dye comprising a condensed poly-ring compound including an azole compound or imidazole compound, and measuring the fluorescence of the biomolecule sample labeled with the organic EL-dye.

2. The detection method according to claim 1, wherein said biomolecule sample is a nucleic acid and said probe is an oligonucleotide or PNA having a base sequence complementary to said nucleic acid.

3. The detection method according to claim 2, wherein said oligonucleotide is a primer or terminator, and the fluorescence measurement is carried out after amplifying the nucleic acid.

4. The detection method according to claim 3, wherein said primer is labeled with the organic EL-dye prior to amplifying the nucleic acid.

5. The detection method according to claim 2, wherein said oligonucleotide or PNA is a molecular beacon.

6. The detection method according to claim 1, wherein said azole compound is a compound of the following general formula (1), (2) or (3):

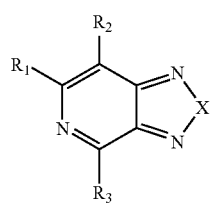

(1)

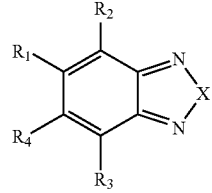

(2)

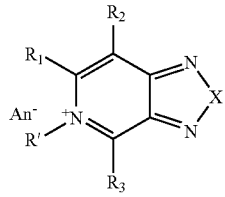

(3)

wherein, $R_1$, $R_2$, $R_3$ and $R_4$ represent each independently an aromatic hydrocarbon group, hydrocarbon group or heterocyclic group, optionally substituted by a halogen atom, hydroxyl group, cyano group or sulfonyl group, and X represents a nitrogen atom, sulfur atom, oxygen atom or selenium atom, R' represents an aliphatic hydrocarbon group optionally substituted by an aromatic ring or aromatic hydrocarbon group and A represents an ionic group comprising halide ion, $CF_3SO_3^-$, $BF_4^-$, or $PF_6^-$.

7. The detection method according to claim 6 wherein the aromatic ring is an aromatic hydrocarbon group.

8. The detection method according to claim 1, wherein said imidazole compound is a compound of the following general formula (4), (5), (6), (7) or (8):

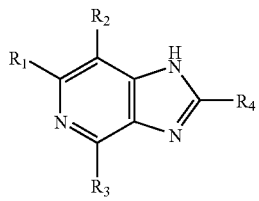

(4)

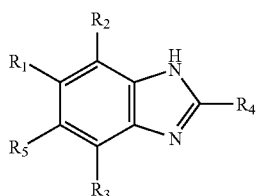

(5)

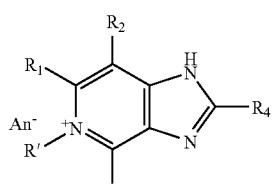

(6)

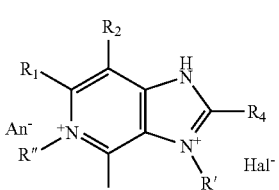

(7)

-continued

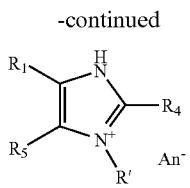
(8)

wherein, each of $R_1$, $R_2$, $R_3$ and $R_4$ and $R_5$ represents each independently an aromatic hydrocarbon group, aliphatic hydrocarbon group or heterocyclic group, optionally substituted by a halogen atom, hydroxyl group, cyano group or sulfonyl group, R' and R" represent an aliphatic hydrocarbon group optionally substituted by an aromatic ring and An⁻ represents an ionic group comprising halide ion, $CF_3SO_3^-$, $BF_4^-$, or $PF_6^-$.

9. The detection method according to claim 8 wherein the aromatic ring is an aromatic hydrocarbon group.

10. A method of detecting a biomolecule, comprising size separating a biomolecule sample by electrophoresis, wherein the biomolecule sample is labeled with an organic EL-dye comprising a condensed poly-ring compound including an azole compound or imidazole compound prior to the electrophoresis or after the electrophoresis.

11. The detection method according to claim 10, wherein said biomolecule sample is a nucleic acid and base sequence(s) of the nucleic acid is determined based on the electrophoresis image of the labeled nucleic acid.

12. The detection method according to claim 10, wherein said biomolecule sample is a protein and the protein removed from the sample based on the electrophoresis image is identified by mass analysis.

13. The detection method according to claim 10, wherein said azole compound is a compound of the following general formula (1), (2) or (3):

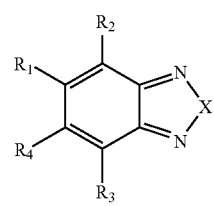
(1)

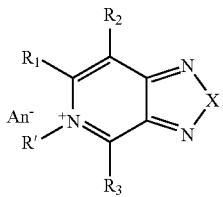
(2)

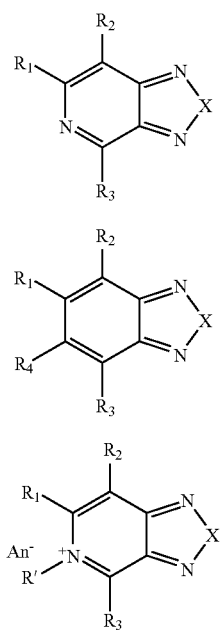
(3)

wherein, $R_1$, $R_2$, $R_3$ and $R_4$ represent each independently an aromatic hydrocarbon group, hydrocarbon group or heterocyclic group, optionally substituted by a halogen atom, hydroxyl group, cyano group or sulfonyl group, and X represents a nitrogen atom, sulfur atom, oxygen atom or selenium atom, optionally having a substituent, R' represents an aliphatic hydrocarbon group optionally substituted by an aromatic ring or aromatic hydrocarbon group and An⁻ represents an ionic group comprising halide ion, $CF_3SO_3^-$, $BF_4^-$, or $PF_6^-$.

14. The detection method according to claim 13 wherein the aromatic ring is an aromatic hydrocarbon group.

15. The detection method according to claim 10, wherein said imidazole compound is a compound of the following general formula (4), (5), (6), (7) or (8):

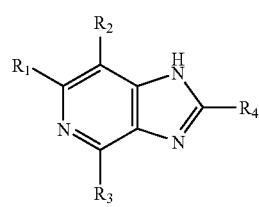
(4)

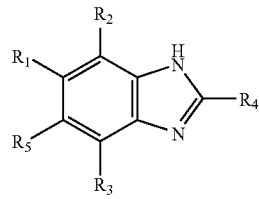
(5)

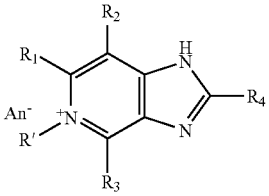
(6)

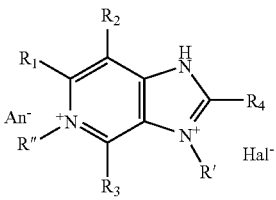
(7)

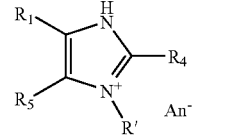
(8)

wherein, each of $R_1$, $R_2$, $R_3$, $R_4$ and $R_5$ represents each independently an aromatic hydrocarbon group, aliphatic hydrocarbon group or heterocyclic group, optionally substituted by a halogen atom, hydroxyl group, cyano group or sulfonyl group, R' and R" represent an aliphatic hydrocarbon group optionally substituted by an aromatic ring and An⁻ represents an ionic group comprising halide ion, $CF_3SO_3^-$, $BF_4^-$, or $PF_6^-$.

16. The detection method according to claim 15 wherein the aromatic ring is an aromatic hydrocarbon group.

* * * * *